US012297239B2

(12) United States Patent
Masson et al.

(10) Patent No.: US 12,297,239 B2
(45) Date of Patent: May 13, 2025

(54) *E. COLI* DEFICIENT IN LON AND SulA FOR GENE TARGETING

(71) Applicant: NATIONAL RESEARCH COUNCIL OF CANADA, Ottawa (CA)

(72) Inventors: Luke Masson, Dollard-des-Ormeaux (CA); Melanie Arbour, Ste-Marthe-sur-le-Lac (CA)

(73) Assignee: National Research Council of Canada, Ottawa (CA)

( * ) Notice: Subject to any disclaimer, the term of this patent is extended or adjusted under 35 U.S.C. 154(b) by 0 days.

(21) Appl. No.: 18/325,199

(22) Filed: May 30, 2023

(65) Prior Publication Data

US 2023/0331788 A1 Oct. 19, 2023

Related U.S. Application Data

(62) Division of application No. 16/639,167, filed as application No. PCT/IB2018/056201 on Aug. 16, 2018, now Pat. No. 11,702,456.

(60) Provisional application No. 62/718,854, filed on Aug. 14, 2018.

(30) Foreign Application Priority Data

Aug. 17, 2017 (EP) .................................... 17186713

(51) Int. Cl.
| | |
|---|---|
| *C07K 14/34* | (2006.01) |
| *C07K 1/22* | (2006.01) |
| *C12N 15/70* | (2006.01) |
| *C12N 15/90* | (2006.01) |

(52) U.S. Cl.
CPC ................ *C07K 14/34* (2013.01); *C07K 1/22* (2013.01); *C12N 15/70* (2013.01); *C12N 15/902* (2013.01); *C07K 2319/034* (2013.01); *C07K 2319/55* (2013.01); *C12N 2500/24* (2013.01); *C12N 2500/34* (2013.01); *C12N 2500/35* (2013.01); *C12N 2500/74* (2013.01)

(58) Field of Classification Search

CPC .................................................. C12N 15/902

See application file for complete search history.

(56) References Cited

U.S. PATENT DOCUMENTS

2013/0029377 A1 1/2013 Caparon et al.

FOREIGN PATENT DOCUMENTS

| | | |
|---|---|---|
| CN | 100999548 A | 7/2007 |
| CN | 101265288 A | 9/2008 |

OTHER PUBLICATIONS

*E. coli* Strain K-12 W3110:JW0941 in KEGG. Retrieved from < https://www.genome.jp/dbget-bin/www_bget?ecj:JW0941 > on Dec. 18, 2024.*
Okshevsky et al., "Efficiency of CRISPR-Cas9 genetic engineering in *Escherichia coli* BL21 is impaired by lack of Lon protease", Journal of Microbiological Methods, 204, 2023, 106648. 4 pages.*
Fang Ting et al, "Expression, purification and characterization of diphtheria toxin mutant CRM197 in *E. coli*", Chinese Journal of Biotechnology, vol. 34, No. 4, pp. 561-568, publication date: Apr. 25, 2018.
Caparon, Maire H., et al. "Integrated solution to purification challenges in the manufacture of a soluble recombinant protein in *E. coli*." Biotechnology and bioengineering 105.2 (2010): 239-249.
Miller W. A.: "P143: Gene Deletion Approach for Improving Apolipoprotein A-1(milano) Purification and Maintaining High Recombinant Protein Expression in *Escherichia coli*", Society for Industrial Microbiology 60th Annual Meeting, Aug. 1, 2010 (Aug. 1, 2010), XP003031984.

* cited by examiner

*Primary Examiner* — Suzanne M Noakes
(74) *Attorney, Agent, or Firm* — Jessica Smith

(57) ABSTRACT

An expression system and process for the production of Diphtheria toxin polypeptides or mutated forms thereof, such as the toxoid CRM197 polypeptide, in genetically-modified *E. coli* with high yield is described. The system and process is based on the uncoupling of biomass growth from recombinant protein induction, i.e. using an inducer of protein production that cannot be used as a carbon source for growth by the bacteria. The use of specific components and conditions that improve protein yields are also described.

9 Claims, 18 Drawing Sheets

Specification includes a Sequence Listing.

```
  1 msrklfasil igallgigap psahagaddv vdssksfvme nfssyhgtkp gyvdsiqkgi
 61 qkpksgtqgn ydddwkgfys tdnkydaagy svdnenplsg kaggvvkvty pgltkvlalk
121 vdnaetikke lglslteplm eqvgteefik rfgdgasrvv lslpfaegss sveyinnweq
181 akalsvelei nfetrgkrgq damyeymaqa cagnrvrrsv gsslscinld wdvirdktkt
241 kieslkehgp iknkmsespn ktvseekakq yleefhqtal ehpelselkt vtgtnpvfag
301 anyaawavnv aqvidsetad nlekttaals ilpgigsvmg iadgavhhnt eeivaqsial
361 sslmvaqaip lvgelvdigf aaynfvesii nlfqvvhnsy nrpayspghk tqpflhdgya
421 vswntvedsi irtgfqgesg hdikitaent plpiagvllp tipgkldvnk skthisvngr
481 kirmrcraid gdvtfcrpks pvyvgngvha nlhvafhrss sekihsneis sdsigvlgyq
541 ktvdhtkvns klslffeiks
```

FIG. 1A

```
   1 atgagcagaa aactgtttgc gtcaatctta ataggggcgc tactggggat aggggcccca
  61 ccttcagccc atgcaggcgc tgatgatgtt gttgattctt ctaaatcttt tgtgatggaa
 121 aacttttctt cgtaccacgg gactaaacct ggttatgtag attccattca aaaaggtata
 181 caaaagccaa aatctggtac acaggaaat tatgacgatg attggaaagg gttttatagt
 241 accgacaata aatacgacgc tgcgggatac tctgtagata tgaaaaccc gctctctgga
 301 aaagctggag gcgtggtcaa agtgacgtat ccaggactga cgaaggttct cgcactaaaa
 361 gtggataatg ccgaaactat taagaaagag ttaggtttaa gtctcactga accgttgatg
 421 gagcaagtcg gaacggaaga gtttatcaaa aggttcggtg atggtgcttc gcgtgtagtg
 481 ctcagccttc ccttcgctga ggggagttct agcgttgaat atattaataa ctgggaacag
 541 gcgaaagcgt taagcgtaga acttgagatt aattttgaaa cccgtggaaa acgtggccaa
 601 gatgcgatgt atgagtatat ggctcaagcc tgtgcaggaa atcgtgtcag gcgatcagta
 661 ggtagctcat tgtcatgcat aaatcttgat tgggatgtca taagggataa aactaagaca
 721 aagatagagt ctttgaaaga gcatggccct atcaaaaata aaatgagcga agtcccaat
 781 aaaacagtat ctgaggaaaa agctaaacaa tacctagaag aatttcatca aacggcatta
 841 gagcatcctg aattgtcaga acttaaaacc gttactggga ccaatcctgt attcgctggg
 901 gctaactatg cggcgtgggc agtaaacgtt gcgcaagtta tcgatagcga aacagctgat
 961 aatttggaaa agacaactgc tgctctttcg atacttcctg gtatcggtag cgtaatgggc
1021 attgcagacg gtgccgttca ccacaataca gaagagatag tggcacaatc aatagcttta
1081 tcgtctttaa tggttgctca agctattcca ttggtaggag agctagttga tattggtttc
1141 gctgcatata attttgtaga gagtattatc aatttatttc aagtagttca taattcgtat
1201 aatcgtcccg cgtattctcc ggggcataaa acacaaccat tcttcatga cgggtatgct
1261 gtcagttgga cactgttga agattcgata atccgaactg gttttcaagg ggagagtggg
1321 cacgacataa aaattactgc tgaaaatacc ccgcttccaa tcgcggtgt cctactaccg
1381 actattcctg gaaagctgga cgttaataag tccaagactc atatttccgt aaatggtcgg
1441 aaaataagga tgcgttgcag agctatagac ggtgatgtaa cttttgtcg ccctaaatct
1501 cctgtttatg ttggtaatgg tgtgcatgcg aatcttcacg tggcatttca cagaagcagc
1561 tcggagaaaa ttcattctaa tgaaatttcg tcggattcca taggcgttct tgggtaccag
1621 aaaacagtag atcacaccaa ggttaattct aagctatcgc tatttttga aatcaaagc
1681 tga
```

FIG. 1B

MKVKVLSLLVPALLVAGAANAGADDVVDSSKSFVMENFSSYHGTKPGYVDSIQKGIQKPK
SGTQGNYDDDWK<u>E</u>FYSTDNKYDAAGYSVDNENPLSGKAGGVVKVTYPGLTKVLALKVDNA
ETIKKELGLSLTEPLMEQVGTEEFIKRFGDGASRVVLSLPFAEGSSSVEYINNWEQAKAL
SVELEINFETRGKRGQDAMYEYMAQACAGNRVRRSVGSSLSCINLDWDVIRDKTKTKIES
LKEHGPIKNKMSESPNKTVSEEKAKQYLEEFHQTALEHPELSELKTVTGTNPVFAGANYA
AWAVNVAQVIDSETADNLEKTTAALSILPGIGSVMGIADGAVHHNTEEIVAQSIALSSLM
VAQAIPLVGELVDIGFAAYNFVESIINLFQVVHNSYNRPAYSPGHKTQPFLHDGYAVSWN
TVEDSIIRTGFQGESGHDIKITAENTPLPIAGVLLPTIPGKLDVNKSKTHISVNGRKIRM
RCRAIDGDVTFCRPKSPVYVGNGVHANLHVAFHRSSSEKIHSNEISSDSIGVLGYQKTVD
HTKVNSKLSLFFEIKS*

FIG. 2A

ATGAAAGTTAAGGTGTTGTCTTTGTTGGTTCCTGCATTGTTGGTCGCTGGTGCTGCAAATGCGGGT
GCAGATGACGTAGTAGACAGCAGCAAATCGTTCGTTATGGAGAATTTCAGCAGCTACCACGGTACG
AAGCCGGGTTACGTCGATTCTATTCAGAAGGGCATCCAGAAACCGAAGTCCGGTACCCAAGGCAAC
TATGATGACGATTGGAAAGAGTTTTACAGCACCGATAACAAATATGACGCAGCGGGTTATAGCGTT
GATAATGAAAATCCGTTGTCCGGCAAAGCAGGCGGCGTGGTCAAAGTGACCTATCCGGGCCTGACC
AAAGTTCTGGCCCTGAAAGTTGATAACGCGGAAACCATTAAGAAAGAGCTGGGTTTGAGCTTGACG
GAACCGCTGATGGAACAGGTCGGCACGGAAGAGTTCATTAAGCGTTTTGGCGATGGTGCTTCTCGC
GTTGTTCTGAGCTTGCCGTTTGCGGAAGGTAGCAGCAGCGTCGAATACATTAACAATTGGGAGCAG
GCGAAAGCCCTGTCCGTTGAGCTGGAGATCAACTTCGAAACCCGCGGTAAGCGTGGCCAAGACGCC
ATGTATGAGTATATGGCCCAAGCGTGTGCTGGCAACCGTGTGCGTCGCAGCGTCGGTAGCAGCCTG
TCGTGTATCAATCTGGATTGGGACGTGATTCGCGACAAAACCAAGACCAAAATCGAAAGCCTGAAA
GAACACGGTCCGATTAAGAATAAGATGAGCGAATCTCCGAATAAGACGGTTAGCGAAGAGAAGGCG
AAACAGTACCTGGAAGAGTTTCACCAGACTGCGCTGGAACATCCAGAGCTGAGCGAGCTGAAAACG
GTGACCGGTACCAACCCAGTTTTTGCTGGTGCGAACTATGCGGCTTGGGCGGTCAACGTGGCACAA
GTCATTGACTCCGAAACGGCAGATAACCTGGAGAAAACCACTGCGGCGCTGAGCATCTTGCCGGGT
ATTGGCAGCGTGATGGGCATCGCGGACGGTGCCGTACACCATAACACCGAAGAGATCGTGGCGCAG
AGCATCGCGCTGAGCTCTCTGATGGTCGCTCAGGCGATCCCGCTGGTGGGTGAGCTGGTTGATATT
GGTTTTGCTGCTTACAACTTTGTTGAGAGCATCATCAATCTGTTCCAGGTGGTGCACAATAGCTAC
AATCGTCCGGCGTACAGCCCTGGTCACAAAACGCAACCGTTCCTGCACGACGGTTACGCGGTTTCC
TGGAATACCGTTGAGGACAGCATTATTCGCACCGGTTTCCAAGGCGAGTCTGGCCATGACATTAAG
ATCACGGCAGAAAACACCCCGCTGCCGATTGCGGGTGTCCTGCTGCCGACGATTCCGGGCAAGCTG
GATGTGAATAAGAGCAAGACCCACATTAGCGTTAACGGCCGTAAGATCCGTATGCGTTGCCGTGCG
ATTGACGGTGACGTGACCTTTTGCCGCCCTAAAAGCCCGGTCTACGTGGGTAATGGTGTGCATGCG
AATCTGCACGTTGCCTTCCATCGTAGCAGCTCCGAGAAAATTCACAGCAATGAGATCAGCTCCGAC
AGCATCGGTGTCCTGGGCTATCAAAAGACCGTCGATCATACGAAGGTTAACTCCAAGCTGAGCTTG
TTCTTTGAGATCAAAAGCTAA

FIG. 2B atgacctttcgcaattgtgtcgccgtcgatctcggcgcatccagtgggcgcgtgatgctggcgcgt
tacgagcgtgaatgccgcagcctgacgctgcgcgaaatccatcgttttaacaatgggctgcatagt
cagaacggctatgtcacctgggatgtggatagcctggaaagtgccattcgccttggattaaacaag
gtgtgcgaggaagggattcgtatcgcgatagcattgggattgatacctggggcgtggactttgtgc
tgctcgaccaacagggtcagcgtgtgggcctgcccgttgcttatcgcgatagccgcaccaatggcc
taatggcgcaggcacaacaacaactcggcaaacgcgatatttatcaacgtagcggcatccagtttc
tgcccttcaatacgctttatcagttgcgtgcgctgacggagcaacaacctgaacttattccacaca
ttgctcacgctctgctgatgccggattacttcagttatcgcctgaccggcaagatgaactgggaat
ataccaacgccacgaccacgcaactggtcaatatcaatagcgacgactgggacgagtcgctactgg
cgtggagcggggccaacaaagcctggtttggtcgcccgacgcatccgggtaatgtcataggtcact
ggatttgcccgcagggtaatgagattccggtggtcgccgttgccagccatgataccgccagcgcgg
ttatcgcctcgccgttaaacggttcacgcgccgcttatctctcttctggcacctggtcattgatgg
gcttcgaaagccagacgccatttaccaatgacacggcgctggcagccaacatcaccaatgaaggcg
gggcggaaggtcgctatcgggtgctgaaaaatattatgggcttatggctgcttcagcgagtgctac
aggagcggcaaatcaacgatctcccggcgcttatcgccgcgacacaggcacttccggcctgccgct
tcatcatcaatcccaatgacgatcgctttattaaccctgacgagatgtgcagcgaaattcaggctg
cgtgtcgggaaatggcgcaaccgatcccagaaagtgatgctgaactggcgcgctgtattttcgaca
gtctggcgttgctgtatgccgatgtgttgcatgagctggcgcagctacgcggtgaagatttctcgc
aactgcatattgtcggcggcggctgccagaacacgctgctcaaccagctatgtgccgatgcctgcg
gtattcgggtgatcgccgggcctgttgaagcctcgacgctcggcaatatcggcatccagttaatga
cgctggatgaactcaacaatgtggatgatttccgtcaggtcgtcagcaccaccgcgaatctgacca
cctttacccctaatcctgacagtgaaattgcccactatgtggcgctgattcactctacacgacaga
caaaggagct

FIG. 11

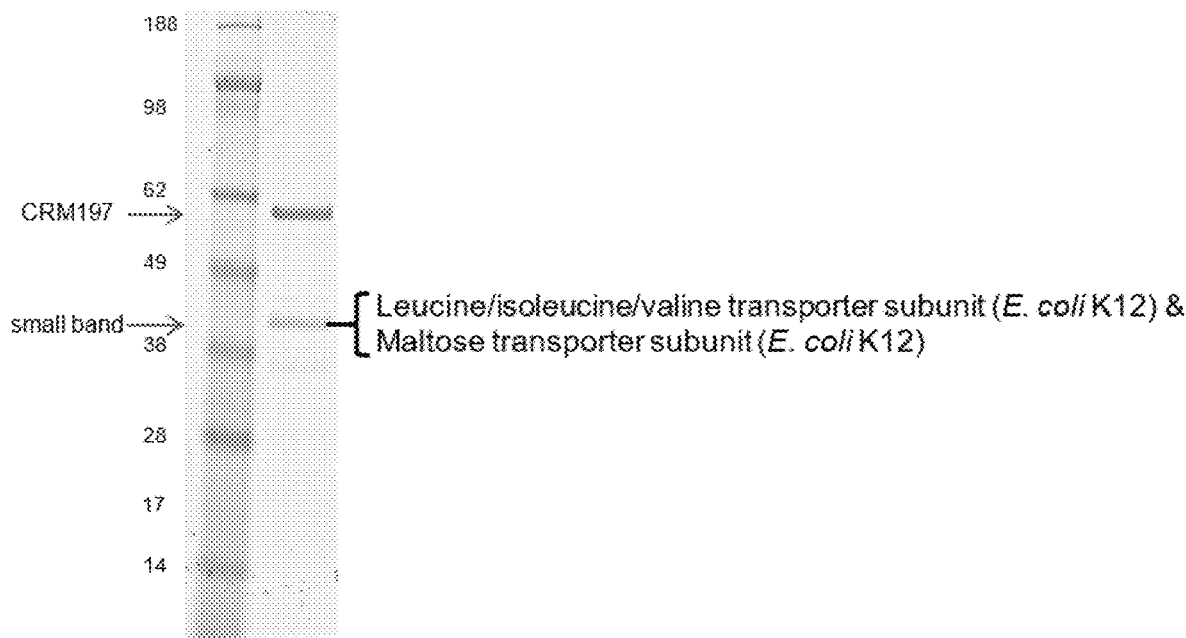

FIG. 12

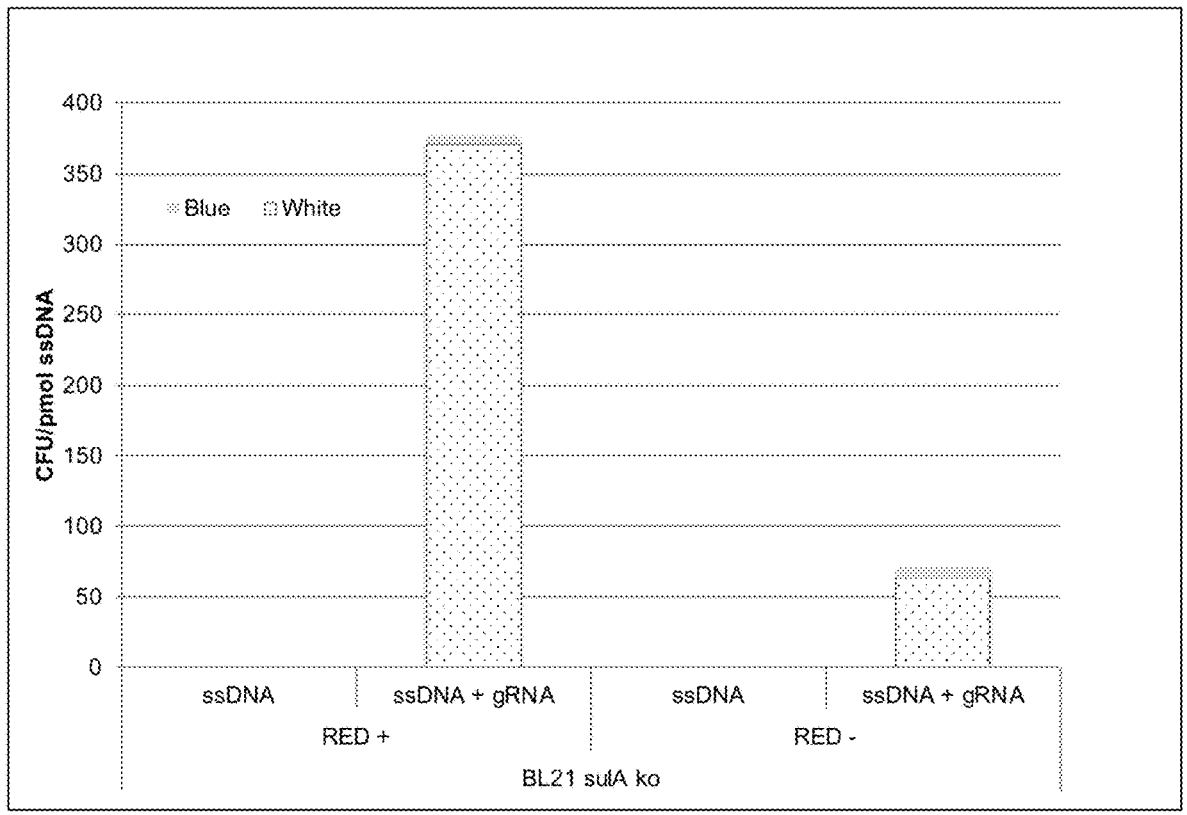

FIG. 19

```
  1  M  Y  T  S  G  Y  A  H  R  S  S  S  F  S  S  A  A  S  K  I
  1  ATGTACACTTCAGGCTATGCACATCGTTCTTCGTCGTTCTCATCCGCAGCAAGTAAAATT

21  A  R  V  S  T  E  N  T  T  A  *  T  *
 61  GCGCGTGTCTCTACGGAAAACACTACAGCCTGAACCTGACAGTGAAGTTGTCTATCGCGA

121  AGATCAGCCCATGATGACGCAACTTCTACTGTTGCCATTGTTACAGCAACTCGGTCAGCA

181  ATCGCGCTGGCAACTCTGGTTAACACCGCAACAAAAACTGAGTCGGGAATGGGTTCAGGC

241  ATCTGGGCTACCCTTAACGAAAGTAATGCAGATTAGCCAGCTCTCCCCTTGCCACACTGT

301  GGAGTCAATGGTTCGCGCTTTACGCACGGGCAATTACAGTGTGGTGATCGGTTGGTTGGC

361  AGATGATTTGACTGAAGAAGAGCATGCTGAACTTGTTGATGCGGCAAATGAAGGTAACGC

421  TATGGGGTTTATTATGCGTCCGGTAAGCGCATCCTCTCACGCCACGAGACAACTTTCCGG

481  GCTAAAAATTCACTCTAATTTGTATCATTAA
```

FIG. 20

E. COLI DEFICIENT IN LON AND SulA FOR GENE TARGETING

CROSS REFERENCE TO RELATED APPLICATIONS

This application is a division of U.S. patent application Ser. No. 16/639,167, filed Feb. 14, 2020, which is a national stage entry of PCT application number PCT/IB2018/056201, filed Aug. 16, 2018, which claims the benefits of EP application Ser. No. 17/186,713.8, filed on Aug. 17, 2017, and U.S. provisional application No. 62/718,854, filed on Aug. 14, 2018, the contents of each of which is incorporated herein by reference in its entirety.

CROSS-REFERENCE TO A SEQUENCE LISTING

The contents of the electronic sequence listing (2017-025-10_SL_ST26.xml; Size: 16,895 bytes; and Date of Creation: May 26, 2023) is herein incorporated by reference in its entirety.

TECHNICAL FIELD

The present invention generally relates to the production of diphtheria toxin polypeptides, for example native diphtheria toxin polypeptide or a variant thereof such as the carrier protein for conjugate vaccine CRM197.

BACKGROUND

Diphtheria toxin (DTx) is a proteinaceous toxin that is synthesized and secreted by toxigenic strains of *Corynebacterium diphtheriae* as a single polypeptide chain of 535 amino acids containing an A (active) domain and a B (binding) domain linked together by a disulfide bridge. The toxin binds to a cell receptor (HB-EGF receptor) and enters the cell by endocytosis where the A domain is released from the B domain by proteolytic cleavage. The A domain then exits the endosome through pores made by the B domain and enters the cytoplasm where it inhibits protein synthesis ultimately resulting in cell death.

Diphtheria is an infection caused by the bacterium *Corynebacterium diphtheriae*. The symptoms and complications (including myocarditis and neuritis) are due to DTx produced by the bacteria. Protection against diphtheria is achieved by vaccination using a diphtheria toxoid, i.e., an inactivated form of DTx obtained by treatment with formaldehyde (formalin), combined with an adjuvant (aluminium salts). The diphtheria vaccine is delivered in several combinations, one including the tetanus toxoid (known as the DT vaccine) and another one including the tetanus and pertussis vaccines, known as the DPT vaccine.

Cross-reacting material 197 (CRM197) is a mutated form of Dtx containing a single amino acid substitution (G52E) that renders the protein enzymatically inactive and non-toxic. CRM197 has been found to be an ideal carrier for conjugate vaccines against encapsulated bacteria. Conjugate vaccines comprise CRM197 covalently linked to poorly immunogenic and T-cell independent capsular polysaccharides, thus creating conjugate antigens that are highly immunogenic and result in long-lasting immunity against the antigen(s). Vaccines containing CRM197 as a carrier protein include vaccines against *Neisseria meningitidis* such as Menveo®, Menjugate®, Meningitec®; vaccines against *Haemophilus influenzae* type B (Hib) such as Vaxem-Hib® and HibTITER®; and pneumococcal vaccines such as Prevnar™.

Diphtheria toxin polypeptides such as CRM197 are difficult to produce in large quantities (>0.2 grams per liter) using the native host strain *Corynebacterium diptheriae*. In addition, the purified protein can be unstable and can degrade rapidly after freeze-thawing. Current production in the native species *Corynebacterium diptheriae* results in about 100-200 mg of CRM197 per liter during fermentation. Yields of about 1.2-1.3 g/L have been reported in a *Pseudomonas fluorescens* strain (PCT publication No. WO 2011/123139). Although an insoluble form of CRM197 can be fermented in *E. coli* to relatively moderate yields, only a fraction of the insoluble product can be converted to the soluble form (Stefan et al., J Biotechnol. 2011 Dec. 20; 156(4):245-52, 2011).

Another major problem is that the commercial protein is very costly (up to $100,000 per gram of purified protein).

There is thus a need for systems and methods to produce soluble, functional and stable diphtheria toxin polypeptides such as DTx and CRM197 at higher yields.

The present description refers to a number of documents, the content of each of which is herein incorporated by reference in its entirety to the same extent as if each individual publication, patent or patent application was specifically and individually indicated to be incorporated by reference in its entirety. Where a term in the present application is found to be defined differently in a document incorporated herein by reference, the definition provided herein is to serve as the definition for the term.

SUMMARY

The present invention relates to systems, methods and products for the production of diphtheria toxin polypeptides or mutated forms thereof.

In various aspects and embodiments, the present disclosure provides the following items 1 to 59:

1. An expression system for producing a Diphtheria toxin polypeptide or a mutated form thereof, the expression system comprising:
   an *Escherichia coli* cell defective in rhamnose catabolic pathway, said *Escherichia coli* cell comprising a heterologous nucleic acid construct comprising:
   (i) a rhamnose inducible promoter sequence; and
   (ii) an expression sequence, said expression sequence comprising a first portion and a second portion, said first portion comprising a nucleotide sequence that encodes a periplasmic secretion signal linked to the 5' end of the second portion, and said second portion comprising a nucleotide sequence that encodes said Diphtheria toxin polypeptide or mutated form thereof, and wherein said expression sequence is operatively linked to said rhamnose inducible promoter sequence.
2. The expression system of item 1, wherein said second portion comprises a nucleotide sequence that encodes said Diphtheria toxin polypeptide.
3. The expression system of item 1, wherein said second portion comprises a nucleotide sequence that encodes said mutated form of Diphtheria toxin polypeptide.
4. The expression system of item 3, wherein said mutated form of Diphtheria toxin polypeptide is CRM197.
5. The expression system of any one of items 1 to 4, wherein said periplasmic secretion signal comprises the amino acid sequence MKVKVLSLLVPALL-VAGAANA (SEQ ID NO:1), or a sequence having at least 90% identity with the sequence of SEQ ID NO:1 that functions as a periplasmic secretion signal.
6. The expression system of any one of items 1 to 5, wherein said nucleotide sequence that encodes said Diphtheria toxin polypeptide or mutated form thereof is an optimized sequence for expression in *Escherichia coli*.
7. The expression system of item 6, wherein said optimized sequence has at least 95% identity with a native nucleotide sequence encoding said Diphtheria toxin polypeptide or mutated form thereof, for example the sequence of SEQ ID NO:2.
8. The expression system of any one of items 1 to 7, wherein said *E. coli* cell is an *E. coli* B strain cell.
9. The expression system of item 9, wherein said *E. coli* B strain cell is an *E. coli* BL21 strain cell.
10. The expression system of any one of items 1 to 9, wherein said rhamnose inducible promoter is a rhaP$_{BAD}$ promoter.
11. The expression system of item 10, wherein said rhaP$_{BAD}$ promoter comprises the nucleotide sequence:

```
                                      (SEQ ID NO: 4)
CACCACAATTCAGCAAATTGTGAACATCATCACGTTCATCTTTCCCTGG
TTGCCAATGGCCCATTTTCCTGTCAGTAACGAGAAGGTCGCGAATTCAG
GCGCTTTTTAGACTGG.
```

12. The expression system of any one of items 1 to 11, wherein said defective rhamnose catabolic pathway is caused by inactivation of a gene encoding a polypeptide involved in said rhamnose catabolic pathway.
13. The expression system of item 12, wherein said polypeptide involved in said rhamnose catabolic pathway is L-rhamnulose kinase (RhaB).
14. The expression system of any one of items 1 to 13, wherein said *Escherichia coli* cell comprises a defective rhamnose transporter (rhaT) gene.
15. The expression system of any one of items 1 to 14, wherein said *Escherichia coli* cell comprises a defective maltose transporter subunit (malE) gene.
16. The expression system of any one of items 1 to 15, wherein said *Escherichia coli* cell expresses a leucine/isoleucine/valine transporter subunit (LivK) fused to an affinity tag.
17. The expression system of item 16, wherein said affinity tag is a histidine tag.
18. The expression system of any one of items 1 to 17, wherein said *E. coli* cell comprises a defective sulA gene.
19. A method for producing a Diphtheria toxin polypeptide or a mutated form thereof, the method comprising:
    (a) culturing the *E. coli* cell defined in any one of items 1 to 18 in a culture medium comprising a carbon source other than rhamnose until an optical density at 600 nm (OD$_{600}$) of at least about 150 is reached;
    (b) adding rhamnose to the culture and feeding the culture with a solution comprising a carbon source for a period of time sufficient to produce said Diphtheria toxin polypeptide or mutated form thereof; and
    (c) collecting the Diphtheria toxin polypeptide or mutated form thereof produced from the periplasm of said cell.
20. The method of item 19, wherein the culturing step (a) is performed until an OD$_{600}$ of at least about 180, or an OD$_{600}$ from about 180 to about 220, is reached.
21. The method of item 19 or 20, wherein the culture medium comprises from about 0.1 g/L to about 100 g/L, or about 5 g/L to about 50 g/L, of a yeast extract.
22. The method of any one of items 19 to 21, wherein the culture medium comprises an iron source at a concentration of at least about 0.001 g/L.
23. The method of any one of items 19 to 22, wherein the length of culture step (a) is about 24 hours to about 32 hours, or about 26 hours to about 30 hours, for example about 28 hours.
24. The method of any one of items 19 to 23, wherein the culture step (a) comprises a first phase and a second phase.
25. The method of item 24, wherein in the first phase the culture medium comprises glucose at a concentration of about 10 g/L to about 30 g/L, or about 20 g/L.
26. The method of item 24 or 25, where the length of the first phase is about 8 hours to about 16 hours, about 10 hours to about 14 hours, or about 12 hours.
27. The method of any one of items 24 to 26, wherein the second phase comprises feeding the culture with a feed solution comprising said carbon source other than rhamnose, for example glucose.
28. The method of item 27, where the feeding flow rate is from about 2 mL/L/h to about 50 mL/L/h, or about 5 mL/L/h to about 40 mL/L/h.
29. The method of item 28, where the feeding flow rate is increased over time.
30. The method of any one of items 27 to 29, wherein the feeding is for a period of about 8 hours to about 20 hours, about 12 hours to about 20 hours, or about 16 hours.
31. The method of any one of items 27 to 30, where the feed solution comprises glucose at a concentration of about 400 g/L to about 800 g/L, or about 650 g/L.
32. The method of any one of items 19 to 31, wherein the rhamnose is added at a concentration of about 0.01% to about 0.2%, about 0.01% to about 0.1%, or about 0.05%.
33. The method of any one of items 19 to 32, wherein the length of step (b) is about 4 hours to about 8 hours, or about 6 hours.
34. The method of any one of items 19 to 33, wherein the feed solution of step (b) comprises glycerol as the carbon source.
35. The method of item 34, where the glycerol is at a concentration of about 400 g/L to about 800 g/L, or about 665 g/L.
36. The method of any one of items 19 to 35, wherein the feeding flow rate in step (b) is from about 5 mL/L/h to about 30 mL/L/h, about 10 mL/L/h to about 20 mL/L/h, or about 14 mL/L/h.
37. The method of any one of items 19 to 36, wherein step (a) and/or step (b) are performed at a temperature of about 20° C. to about 30° C., or about 26° C.
38. The method of any one of items 19 to 37, wherein the culture in step (a) and/or step (b) has a pH of about 6.0 to about 7.0, or about 6.8.
39. The method of any one of items 19 to 38, wherein steps (a) and (b) are performed in a fermentation bioreactor.
40. The method of any one of items 19 to 39, further comprising purifying the Diphtheria toxin polypeptide or mutated form thereof collected in step (c).

41. The method of item 40, wherein said purifying comprises ion-exchange chromatography and/or hydrophobic interaction chromatography and/or mixed-mode chromatography.
42. The method of item 41, wherein said purifying comprises affinity chromatography.
43. The method of any one of items 19 to 42, wherein the yield of soluble Diphtheria protein or mutated form thereof is at least 2.0 g per litre of culture.
44. The method of item 43, wherein the yield of soluble Diphtheria protein or mutated form thereof is at least 3.0 g per litre of culture.
45. The method of item 43, wherein the yield of soluble Diphtheria protein or mutated form thereof is at least 4.0 g per litre of culture.
46. An *Escherichia coli* cell comprising a defective sulA gene and a defective Ion gene.
47. The *E. coli* cell of item 46, wherein the *E. coli* cell is a BL21 strain cell.
48. The *E. coli* cell of item 47, wherein the *E. coli* cell is a BL21(DE3) strain cell.
49. The *E. coli* cell of any one of items 46 to 48, wherein the cell is defective in rhamnose catabolic pathway.
50. The *E. coli* cell of item 49, wherein the cell comprises a defective rhaB gene.
51. The *E. coli* cell of any one of items 46 to 50, wherein the defective sulA gene comprises the nucleotide sequence set forth in SEQ ID NO: 10.
52. Use of the *E. coli* cell of any one of items 46 to 51 for gene targeting by homologous recombination.
53. A method of gene targeting by homologous recombination, the method comprising introducing an in vivo double-strand break into a DNA molecule within an *E. coli* cell of any one of items 46 to 50, in the presence of a donor substrate DNA molecule.
54. The method of item 53, wherein the double-strand break is introduced using a CRISPR-Cas system.
55. An expression system comprising the *E. coli* cell of any one of items 46 to 50, wherein the *E. coli* cell comprises a heterologous nucleic acid construct comprising an inducible promoter sequence operably linked to a nucleic acid molecule encoding a polypeptide.
56. The expression system of item 55, wherein the inducible promoter is a rhamnose inducible promoter.
57. A method for increasing the amenability of an *E. coli* cell that is void of Lon protease to gene targeting by homologous recombination, the method comprising introducing into the *E. coli* cell a genetic alteration that reduces the function of the sulA gene in the *E. coli* cell.
58. The method of item 57, wherein the *E. coli* cell is a BL21 strain cell.
59. The method of item 57 or 58, wherein the *E coli* cell is defective in rhamnose catabolic pathway.

Other objects, advantages and features of the present invention will become more apparent upon reading of the following non-restrictive description of specific embodiments thereof, given by way of example only with reference to the accompanying drawings.

BRIEF DESCRIPTION OF DRAWINGS

In the appended drawings:

FIG. 1A shows the amino acid sequence of native diphtheria toxin (DTx), with the signal peptide in bold and underlined (SEQ ID NO:7).

FIG. 1B shows the nucleotide sequence encoding native diphtheria toxin (DTx), with the sequence encoding the signal peptide in bold and underlined (SEQ ID NO:6).

FIG. 2A shows the amino acid sequence of the chimeric CRM197 polypeptide used in the studies described herein (SEQ ID NO:3). The sequence of the OmpC secretion signal peptide, which replaces the native signal peptide of DTx, is in bold and underlined. The glutamic acid (E) residue corresponding to the substitution (G52E) that renders the CRM197 protein enzymatically inactive and non-toxic is underlined.

FIG. 2B shows the nucleotide sequence encoding the chimeric CRM197 polypeptide of FIG. 2A, with the sequence encoding the OmpC secretion signal peptide in bold and underlined (SEQ ID NO:2).

FIG. 3A shows an SDS-PAGE gel representing CRM197 production in *E. coli* BL21 ΔrhaB cells comprising CRM197 constructs with different signal sequences cultured in flasks (8% MOPS Bolt Bis-Tris SDS-PAGE, T5 h, OD adjusted on gel). Protein production was induced by addition of 0.1% L-rhamnose, in the presence of 0.05% glucose (early auto-induction).

FIG. 3B shows an SDS-PAGE gel representing CRM197 production in *E. coli* BL21 ΔrhaB cells comprising CRM197 constructs with different signal sequences cultured for 34 h or 36 h in Dasgip reactors (8% MOPS Bolt Bis-Tris SDS-PAGE, OD adjusted on gel).

FIG. 3C is a graph showing the results of a Bradford assay and gel densitometry analysis depicting the CRM197 yields using OmpT and OmpC signal sequences (at 34 h).

FIG. 4A is a graph showing the growth of *E. coli* BL21 ΔrhaB cells cultured with a feed solution comprising glycerol (diamonds) or glucose (circles) as the carbon source.

FIG. 4B is a graph showing the concentration of CRM197 protein in the periplasm of *E. coli* BL21 ΔrhaB cells cultured with a feed solution comprising glycerol (left bar) or glucose (right bar) as the carbon source.

FIG. 5A is a graph showing the growth of *E. coli* BL21 ΔrhaB cells induced at 24 h (triangles, 4 h before end of fedbatch) or 28 h (squares, end of fedbatch).

FIG. 5B is a graph showing the concentration of CRM197 protein in the periplasm of *E. coli* BL21 ΔrhaB cells cultured for 44 h following induction at 28 h (left bar) or 24 h (right bar).

FIG. 6A is a graph showing the growth of *E. coli* BL21 ΔrhaB cells cultured with (circles) or without (squares) a post-feed solution comprising glycerol.

FIG. 6B is a graph showing the concentration of CRM197 protein in the periplasm of *E. coli* BL21 ΔrhaB cells cultured without (left bar) or with (right bar) a post-feed solution comprising glycerol.

FIG. 7 is a graph showing the concentration of CRM197 protein in the periplasm of *E. coli* BL21 ΔrhaB cells cultured at 26° C. in Dasgip reactors (2.2 L) following induction with different concentrations of L-rhamnose (punctual induction at 28 h).

FIG. 8 is a graph showing the concentration of CRM197 protein in the periplasm of *E. coli* BL21 ΔrhaB cells cultured at 26° C., 28° C. or 30° C. in micro-reactors following induction with L-rhamnose. Left bars=12 h of culture; right bars=24 h of culture.

FIG. 9 is a graph showing the $OD_{600nm}$, after 28 h of culture (time of induction) of *E. coli* BL21 ΔrhaB cells in Dasgip reactors for several fermentation runs.

FIG. 10A shows an SDS-PAGE gel representing CRM197 production in *E. coli* BL21 ΔrhaB cells cultured under the conditions described in Example 6.

FIG. 10B is a graph showing the results of a Bradford assay and gel densitometry analysis depicting the CRM197 yields in *E. coli* BL21 ΔrhaB cells cultured under the conditions described in Example 6.

FIG. 11 shows the sequence of the mutated L-rhamnulokinase (rhaB) gene used in the studies described herein, with the 2-nucleotide insertion causing the frameshift in bold and underlined (SEQ ID NO:8).

FIG. 12 depicts an SDS-PAGE gel of a CRM197 preparation after the first purification step (anion-exchange chromatography) with the arrows showing the CRM197 band and an ~40 kDa contaminating band.

FIG. 19 is a graph showing the number of CFUs obtained after gene targeting of lacZ using CRISPR-lambda RED in a BL21ΔsulA *E. coli* strain.

FIG. 20 shows the nucleotide sequence (SEQ ID NO: 10) of the sulA coding region in the B0023 (BL21 ΔrhaB ΔsulA ΔmalE) strain. The bold, underlined nucleotides were introduced into the sulA locus to create two stop codons, which are shown in the translation provided above the nucleotide sequence.

DETAILED DISCLOSURE

Figure 3A:
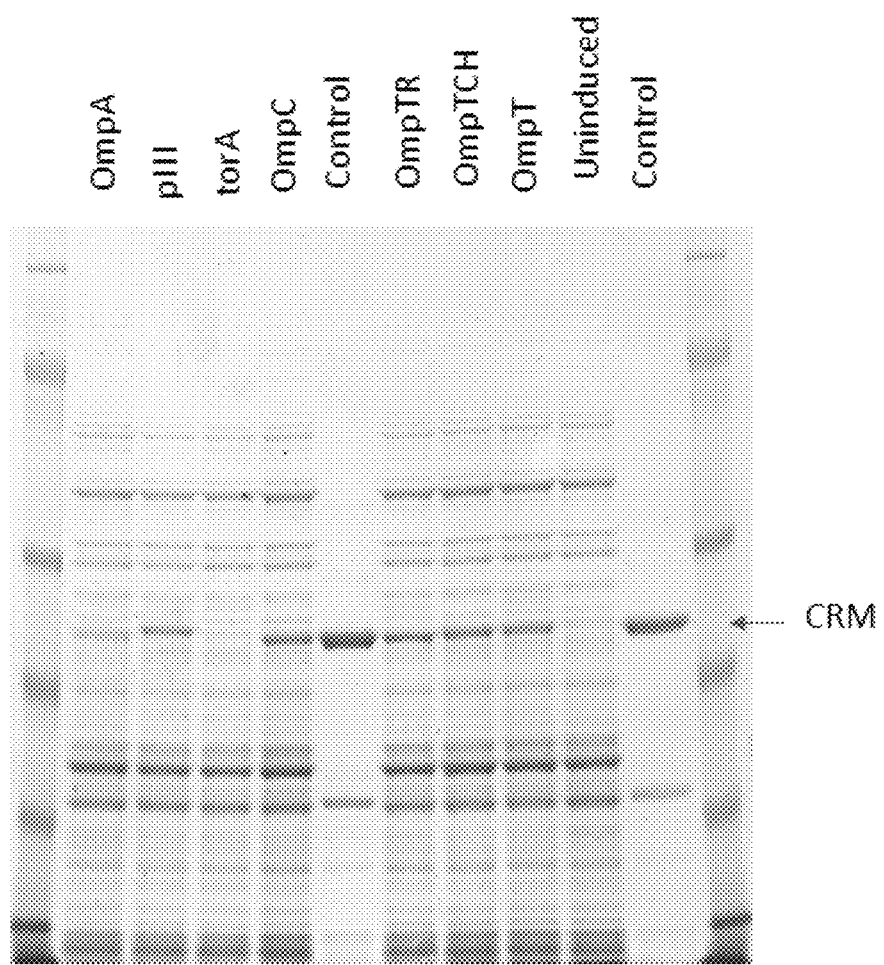

The use of the terms "a" and "an" and "the" and similar referents in the context of describing the invention (especially in the context of the claims) are to be construed to cover both the singular and the plural, unless otherwise indicated herein or clearly contradicted by context.

The terms "comprising", "having", "including", and "containing" are to be construed as open-ended terms (i.e., meaning "including, but not limited to") unless otherwise noted.

Recitation of ranges of values herein are merely intended to serve as a shorthand method of referring individually to each separate value falling within the range, unless otherwise indicated herein, and each separate value is incorporated into the specification as if it were individually recited herein. All subsets of values within the ranges are also incorporated into the specification as if they were individually recited herein.

All methods described herein can be performed in any suitable order unless otherwise indicated herein or otherwise clearly contradicted by context.

The use of any and all examples, or exemplary language (e.g., "such as") provided herein, is intended merely to better illustrate the invention and does not pose a limitation on the scope of the invention unless otherwise claimed.

No language in the specification should be construed as indicating any non-claimed element as essential to the practice of the invention.

Herein, the terms "about" and "approximately" have their ordinary meaning. They are used to indicate that a value includes an inherent variation of error for the device or the method being employed to determine the value, or encompass values close to the recited values, for example within 10% or 5% of the recited values (or range of values).

Unless otherwise defined, all technical and scientific terms used herein have the same meaning as commonly understood by one of ordinary skill in the art to which this invention belongs.

In the studies described herein, the development of an expression system and process for the production of DTx polypeptides in *E. coli* with high yield is described.

Expression System for Producing Diphtheria Toxin Polypeptides or Mutated Forms Thereof Accordingly, in a first aspect, the present disclosure provides an expression system for producing a Diphtheria toxin polypeptide or a mutated form thereof, the expression system comprising:

an *E. coli* host cell defective in rhamnose catabolic pathway, said *E. coli* cell comprising a heterologous nucleic acid construct comprising:
(i) an rhamnose inducible promoter sequence; and
(ii) an expression sequence, said expression sequence comprising a first portion and a second portion, said first portion comprising a nucleotide sequence that encodes a periplasmic secretion signal linked to the 5' end of the second portion, and said second portion comprising a nucleotide sequence that encodes said Diphtheria toxin polypeptide or mutated form thereof, and wherein said expression sequence is operably linked to said rhamnose inducible promoter sequence.

In an embodiment, the *E. coli* host cell is an *E. coli* B strain cell.

In an embodiment, the heterologous nucleic acid construct is comprised in a plasmid or vector, e.g., an expression vector. Thus, in an embodiment, the expression system comprises an *E. coli* cell defective in rhamnose catabolic pathway, the *E. coli* cell comprising a plasmid or vector comprising the heterologous nucleic acid construct defined herein.

The vector may be any vector capable of mediating expression of a heterologous protein in an *E. coli* cell. The vector may be, for example, an autonomously or self-replicating plasmid, a cosmid, a phage, a virus or a retrovirus. Useful expression vectors may consist, for example, of segments of chromosomal, non-chromosomal and/or synthetic nucleic acid sequences. Suitable vectors include vectors with a specific host range such as vectors specific for *E. coli* B strain cells, as well as vectors with a broad host range such as vectors useful for Gram-negative bacteria. "Low-copy", "medium-copy" as well as "high-copy" plasmids can be used. The vector may also comprise a selectable marker, for example a sequence conferring antibiotic resistance (e.g., kanamycin resistance), and an expression cassette.

Examples of useful vectors for expression in *E. coli* include: pQE70, pQE60 and pQE-9 (QIAGEN, Inc.); pBluescript Vektoren, Phagescript Vektoren, pNH8A, pNH16a, pNH18A, pNH46A (Stratagene Cloning Systems, Inc.); ptrc99a, pKK223-3, pKK233-3, pDR540, pRIT5 (Pharmacia Bio-tech, Inc.); pLG338, pACYC184, pBR322, pUC18, pUC19, pKC30, pRep4, pACYC177, pACYC184, pRSF1010 and pBW22 (Wilms et al., 2001, *Biotechnology* and *Bioengineering*, 73 (2) 95-103) or derivatives thereof such as plasmid pBW22-Fab-H or plasmid pAKL14, as well as plasmid pD861 (ATUM, Newark, California). Further useful plasmids are well known to the person skilled in the art and are described, for example, in "Cloning Vectors" (Eds. Pouwels P. H. et al. Elsevier, Amsterdam-New York-Oxford, 1985). In an embodiment, the plasmid is pD861 plasmid.

The present disclosure also relates to the periplasmic expression of recombinant diphtheria toxin polypeptides or mutated forms thereof in an *E. coli* host cell using the systems/processes described herein. The expression of proteins in the periplasm has been used for industrial applications and has been reviewed in Hanahan, *J. Mol. Biol.*, 166:557-580 (1983); Hockney, *Trends Biotechnol.*, 12:456-632 (1994); and Hannig et al., *Trends Biotechnol.*, 16:54-60 (1998). Thus, in embodiments, methods are provided comprising growing an *E. coli* host cell defective in rhamnose catabolic pathway comprising an expression vector comprising a nucleic acid sequence encoding a diphtheria toxin polypeptide or mutated form thereof fused to a periplasmic signal sequence, operably linked to an rhamnose inducible promoter sequence under conditions suitable for the expression of the recombinant diphtheria toxin polypeptide or mutated form thereof. According to these methods, a high yield of intact soluble diphtheria toxin polypeptide or mutated form thereof is produced and substantially all of the soluble diphtheria toxin polypeptide or mutated form thereof can be recovered.

The presence of a periplasmic secretion signal on a protein facilitates the transport of the newly translated protein across the inner membrane of *E. coli* into the periplasmic space. The signal sequence is then cleaved. Accordingly, replacement of the native *C. diphtheriae* signal sequence with a signal sequence that directs transfer of the diphtheria toxin polypeptide or mutated form thereof to the periplasm of *E. coli* (periplasmic secretion signal) ultimately results in a mature protein having the same amino acid sequence. The term "periplasmic secretion signal" as used herein refers to a peptide, typically comprising from about 15 to about 30 amino acid residues, which has the ability to target the diphtheria toxin polypeptide or mutant form thereof to the periplasm of the *E. coli* cells. Periplasmic secretion signal peptides are typically composed of a positively charged amino terminus (n-region), a central hydrophobic core (h-region), and a polar cleavage region (c-region). Examples of periplasmic secretion signal peptides include signal recognition particle (SRP)-dependent signal peptides such as the DsbA, TolB or TorT secretion signal peptides; Sec-dependent signal peptides such as the OmpF, OmpT, OmpC, OmpA, PhoA, MalE, LamB, LivK or PelB secretion signal peptides; and twin arginine translocation (TAT) signal peptides such as the TorA or Sufl secretion signal peptide, or any variant, combination or fusion thereof. In an embodiment, the periplasmic secretion signal peptide comprises or consists of an amino acid sequence having at least 70%, at least 75%, at least 80%, at least 85%, at least 90%, at least 95%, at least 96%, at least 97%, at least 98% or at least 99% identity with the sequence of a native periplasmic secretion signal peptide, for example, among those listed above, and which retains the ability to secrete the diphtheria toxin polypeptide or mutant form thereof to the periplasm of the *E. coli* B strain cells. In an embodiment, the periplasmic secretion signal peptide is a Sec-dependent signal peptide. In a further embodiment the periplasmic signal peptide is an OmpC secretion signal peptide (comprising or consisting of the sequence MKVKVLSLL-VPALLVAGAANA, SEQ ID NO:1, or of a sequence having at least 70%, at least 75%, at least 80%, at least 85%, at least 90%, at least 95%, at least 96%, at least 97%, at least 98% or at least 99% identity with SEQ ID NO: 1). It is to be understood that signal sequences useful in the methods/processes described herein are not limited to those listed above. In an embodiment, the periplasmic secretion signal results in direction of at least about 70%, at least about 80%, at least about 90% or at least about 95% of the polypeptide to the periplasm when expressed in *E. coli*. In an embodiment, the nucleotide sequence encoding the signal sequence is contiguous with, and in the same reading frame as, the nucleotide sequence that encodes the Diphtheria toxin polypeptide or mutated form thereof.

The term "diphtheria toxin polypeptide or a mutated form thereof" refers to the native diphtheria toxin synthesized and secreted by toxigenic strains of *Corynebacterium diphtheriae*, or to a mutated form thereof comprising one or more mutations relative to the sequence of the native diphtheria toxin. In an embodiment, the mutated form has attenuated toxicity relative to the native diphtheria toxin. A well-known mutated form of diphtheria toxin is CRM197, which comprises a glycine to glutamic acid substitution at position 52 (G52E) in fragment A of the native toxin, which results in the loss of ADP-ribosyltransferase activity. Other known mutated forms of diphtheria toxin include CRM30, CRM45, CRM228, CRM107, CRM102, CRM103, CRM9, CRM1001, CRM228 and CRM176 (see, e.g., Johnson and Nicholls, JOURNAL OF BACTERIOLOGY, August 1994, p. 4766-4769). Diphtheria toxin variants, i.e. mutated forms of diphtheria toxin, having reduced binding to vascular endothelium or vascular endothelial cells are disclosed in U.S. Pat. Nos. 7,585,942 and 8,865,866. In an embodiment, the systems and methods defined herein are for producing a native diphtheria toxin polypeptide, and thus the heterologous nucleic acid construct comprises a nucleotide sequence that encodes a native Diphtheria toxin polypeptide. In another embodiment, the systems and methods defined herein are for producing a Diphtheria toxin polypeptide comprising the CRM197 mutation, i.e. a glycine to glutamic acid substitution at position 52 (G52E) in fragment A. In another embodiment, the systems and methods defined herein are for producing a CRM197 polypeptide, and thus the heterologous nucleic acid construct comprises a nucleotide sequence that encodes a CRM197 polypeptide.

The nucleotide sequence of the DTx polypeptide or mutated form thereof for use in the systems and processes described herein may be prepared using recombinant DNA technology. For example, the DTx polypeptide or mutated form thereof can be chemically synthesized or can be prepared based on the known nucleotide sequences of the native gene for diphtheria toxin carried by *Corynebacterium diphtheriae* or of known mutants. In an embodiment, the nucleotide sequence of the DTx polypeptide or mutated form thereof is optimized for expression in *E. coli*. A variety of sequence features of the heterologous nucleic acid can be optimized including, without limitation, modification of translation initiation regions, alteration of mRNA structural elements, and the use of different codon biases. Methods for optimizing nucleic acid sequence to improve expression in *E. coli* host cells are known in the art and described, for example, in U.S. Pat. No. 7,561,972. In an embodiment, the optimized nucleotide sequence comprises at least optimized codons. The presence of codons that are rarely used in *E. coli* may delay translation of the encoded protein and result in a reduced expression in the *E. coli* host cell. Thus, in one aspect, the general codon usage in *E. coli* is used to optimize the expression of the DTx polypeptide or mutated form thereof in *E. coli*. In other embodiments, optimization of the DTx polypeptide or mutated form thereof for expression in *E. coli* also comprises minimization of interfering secondary structure. In an embodiment, the optimized DTx polypeptide or DTx polypeptide mutant sequence is an optimized CRM197 sequence. An exemplary CRM197 nucleotide sequence, optimized for expression in the periplasm of *E. coli* when attached to an upstream region encoding a signal sequence, is provided as SEQ ID NO: 2 (FIG. 2B). Codon-optimized sequences for expression in *E. coli* may be obtained commercially, for example from ATUM (Menlo Park, CA). Additional strategies for optimizing the DTx polypeptide or DTx polypeptide mutant nucleotide sequences for expression in *E. coli* are known in the art and can be used in addition to or as an alternative to the strategies described herein. In an embodiment, the DTx polypeptide or mutated form thereof comprises or consists of an amino acid sequence having at least 70%, at least 75%, at least 80%, at least 85%, at least 90%, at least 95%, at least 96%, at least 97%, at least 98% or at least 99% identity with the sequence of the native mature DTx polypeptide (FIG. 1A) or CRM197 polypeptide (FIG. 2A). In an embodiment, the DTx polypeptide or mutated form thereof comprises or consists of the sequence of the native mature DTx polypeptide (FIG. 1A) or CRM197 polypeptide (FIG. 2A). In an embodiment, the nucleotide sequence that encodes the DTx polypeptide or mutated form thereof has at least 70%, at least 75%, at least 80%, at least 85%, at least 90%, at least 95%, at least 96%, at least 97%, at least 98% or at least 99% identity with a native or optimized nucleotide sequence encoding a DTx polypeptide (e.g., FIG. 1B) or CRM197 polypeptide (e.g., FIG. 2B). In an embodiment, the nucleotide sequence that encodes the DTx polypeptide or mutated form thereof comprises or consists of the nucleotide sequence set forth in FIG. 1B or FIG. 2B.

The *E. coli* strain used in the systems and processes described herein may be any *E. coli* strain, such as a K-12 strain (e.g., MG1655 (ATCC No. 47076) or W3110 (ATCC No. 27325)), or a B strain. In an embodiment, the *E. coli* strain is an *E. coli* B strain.

The term "*E. coli* B strain" refers to the clonal descendants of a *Bacillus coli* strain from the Institut Pasteur (Luria, S E & Anderson, T F, 1942, *Proc. Natl. Acad. Sci. U.S.A.* 28 127-130; Daegelen, P et al., 2009, *J. Mol. Biol.* 394 634-43—NCBI Taxonomy ID 37762). B strains are typically characterized by protease deficiency, low acetate production at a high level of glucose, and enhanced permeability. Representative *E. coli* B strains include the BL21 (BL21AI™, BL21(DE3), BL21 Star™(DE3), BL21-Gold (DE3), BL21(DE3)plys, C41(DE3), C43(DE3), BLR(DE3), B834(DE3 Tuner™ (DE3), ER2566, ER2833, ER3011, ER3012, REL606, ATCC 11303, B-6, B40, BB, Bc251, BE, Br, and CIP 54.125 strains. In an embodiment, the *E. coli* B strain used in the systems and methods described herein is *E. coli* BL21.

The term "rhamnose inducible promoter sequence" refers to a nucleotide sequence that, when operably linked to a gene, induces the expression of the gene in the presence of a suitable amount of rhamnose. Examples of such promoters include the rhamnose promoter rhaSB (WO 2003/068956) and the rhamnose promoter rhaP$_{BAD}$ (WO 2004/050877). In an embodiment, the rhamnose inducible promoter comprises the rhaP$_{BAD}$ promoter region of the L-rhamnose operon. "L-rhamnose operon" refers to the rhaSR-rhaP$_{BAD}$ operon as described for *E. coli* in Holcroft and Egan, 2000, *J. Bacteriol.* 182 (23), 6774-6782. The rha$_{BAD}$ operon is a positively regulated catabolic operon which transcribes RhaB, RhaA and RhaD divergently from another rha operon, rhaSR, with approximately 240 bp of DNA separating their respective transcription start sites. The rhaSR operon encodes the two L-rhamnose-specific activators RhaS and RhaR. RhaR regulates transcription of RhaSR, whereas RhaS binds DNA upstream at −32 to −81 relative to the transcription start site of rhaP$_{BAD}$. Furthermore, the rhaSR-rhaP$_{BAD}$ intergenic operon contains catabolite regulator protein (CRP) binding sites at positions −92.5 (CRP 1) relative to the transcription start site of rhaP$_{BAD}$ and CRP binding sites at positions −92.5 (CRP 2), −115.5 (CRP 3) and 116.5 (CRP 4) relative to the transcription start site of rhaSR as well as a binding site for RhaR spanning −32 to −82 relative to the transcription start site of rhaSR.

The term "rhaP$_{BAD}$ promoter region of the L-rhamnose operon" refers to the rhaP$_{BAD}$ operon consisting essentially of the rhaP$_{BAD}$ transcription initiation site, the putative −35 region, the Pribnow box, the CRP binding site CPR1, the binding site for RhaS relative to the transcription start site of rha$_{BAD}$ as well as CRP binding sites CRP 2-4, and binding site for RhaR relative to the transcription start site of rhaSR. With "rhaP$_{BAD}$ promoter" is meant the promoter of the rhaP$_{BAD}$ operon consisting essentially of the rhaP$_{BAD}$ transcription initiation site, the putative −35 region, the Pribnow box, the binding site for RhaS and the CRP1 binding site region relative to the transcription start site of rhaP$_{BAD}$, and the CRP binding site CRP4 or a part thereof relative to the transcription start site of rhaSR. In an embodiment, the rhamnose inducible promoter comprises or consists of the sequence CACCACAATTCAGCAAATTGTGAACAT-CATCACGTTCATCTTTCCCTGGTTGCCAATGGCCC ATTTTCCTGTCAGTAACGAGAAGGTCGCGAAT-TCAGGCGCTTTTTAGACTGG (SEQ ID NO:4). In another embodiment, the rhamnose inducible promoter comprises or consists of the sequence: CACCACAAT-TCAGCAAATTGTGAACATCATCACGTT-CATCTTTCCCTGGTTGCCAATGGCCC ATTTTCCTGTCAGTAACGAGAAGGTCGCGAAT-TCAGGCGCTTTTTAGACTGGTCGTAATGA ACAATT (SEQ ID NO:5). Expression systems based on the rhamnose promoter are commercially available (e.g., Expresso® Rhamnose promoter system, Cambridge Bioscience, *E. coli* Expression Vectors with the Rhamnose-inducible rha$_{BAD}$ Promoter from ATUM)

A nucleic acid sequence is "operably linked" when it is placed into a functional relationship with another nucleic acid sequence. For example, DNA encoding a signal sequence is operably linked to DNA encoding a protein if it is expressed as part of a preprotein that participates in the secretion of the protein; a promoter is operably linked to a coding sequence if it affects the transcription of the coding sequence; or a translation initiation region such as a ribosome binding site is operably linked to a nucleic acid molecule encoding, for example, a polypeptide if it is positioned so as to facilitate translation of the polypeptide. Linking can be accomplished by ligation at convenient restriction sites. If such sites do not exist, then synthetic oligonucleotide adaptors or linkers may be used in accordance with conventional practice.

In an embodiment, the expression systems or vectors described herein further comprise one or more enhancers. The term "enhancer" refers to a nucleic acid sequence that acts to potentiate the transcription of a transcriptional unit independent of the identity of the transcriptional unit, the position of the enhancer sequence in relation to the transcriptional unit, or the orientation of the enhancer sequence.

It has been found by the present inventors that significantly improved yields can be obtained by uncoupling biomass growth from recombinant protein induction through the use of a E. coli strain defective in rhamnose catabolic pathway (i.e. unable to use rhamnose as a carbon source) together with the use of rhamnose as an inducer of protein production. Accordingly, the E. coli host cell used in the systems and processes described herein is defective in rhamnose catabolic pathway, i.e. has the inability to use rhamnose as a carbon source. This may be achieved by inactivating (e.g., mutating or deleting) one or more genes involved in rhamnose catabolism in the host cell. For example, the three (3) main enzymes involved in rhamnose catabolism in E. coli are: L-Rha isomerase (rhaA), L-rhamnulose kinase (rhaB), and L-rhamnulose-1-phosphate aldolase (rhaD) (see, e.g., Rodionova et al., 2013, Front Microbiol. 2013; 4: 407). Thus, in an embodiment, the E. coli host cell used in the systems and processes described herein has one or more of these 3 genes inactivated. In an embodiment, the E. coli host cell used in the systems and processes described herein has an inactivated or defective L-rhamnulose kinase (rhaB) gene. Inactivation of the gene (s) involved in rhamnose catabolism may be performed using any method, for example by deleting the entire gene(s) or introducing one or more mutations that prevent the expression of a functional protein (e.g., in the coding region or a promoter/enhancer region). For example, inactivation of the rhaB gene (Gene ID: 948399) may be achieved by inserting one or more nucleotides in the coding sequence of the gene to create a detrimental frameshift. In a further embodiment, inactivation of the rhaB gene is achieved by inserting two nucleotides at position 221 of the rhaB gene (SEQ ID NO: 8), thus creating a detrimental frameshift in the sequence.

As used herein, "defective gene" refers to a gene comprising one or more mutations within its coding and/or regulatory regions, the one or more mutations causing a reduction or loss of expression of the gene, or that result in a loss of activity of the gene product or a reduction in the activity of the gene product, relative to the wild-type gene. Such mutations include, for example, deletions, insertions, rearrangements, frame-shift mutations, premature stop codons, and substitutions.

In embodiments, the E. coli host cell additionally comprises one or more modifications than can improve the growth of the cells and/or the production of the DTx polypeptide or mutated form thereof, for example by improving cell metabolism (e.g., decreasing acetate anabolism), decreasing a stress, and the like. Also, the E. coli host cell may be modified to express or overexpress one or more proteins for improving or increasing the translocation and/or folding of the diphtheria toxin polypeptide or mutated form thereof in the periplasm. Nucleic acid(s) comprising a sequence encoding one or more proteins for improving or increasing the translocation and/or folding of the diphtheria toxin polypeptide in the periplasm may be integrated into the host cell's genome, or may be integrated into a plasmid/vector, for example the same expression plasmid/vector comprising the nucleotide sequence encoding the diphtheria toxin polypeptide, or a different expression plasmid/vector. Overexpression of one or more genes of interest may also be achieved by modifying or replacing the native transcriptional control elements (e.g., promoters) controlling the expression of the gene(s) by other transcriptional control elements allowing stronger expression of the gene(s), for example a more potent promoter.

Examples of proteins that may improve or increase the translocation and/or folding of a diphtheria toxin polypeptide are known in the art and include, without limitation, chaperones such as Skp, DnaK, DnaJ, CaflM, and CaflA; proteins involved in disulfide bond formation such as DsbA, DsbB, DsbC and DsbD; peptidyl-prolyl cis-trans isomerases such as PpiA, PpiD, FkpA and SurA; soluble partner proteins such as MBP, GST, and thioredoxin; proteins involved in secretion pathways such as YebF, MalE, HlyA, Hirudin, OmpF, and Spy; protease inhibitors such as YccA; and proteins that relieve export saturation such as PspA. In embodiments, the E. coli host cell may also be modified by deleting or knocking down genes encoding proteins that may adversely affect the production of the DTx polypeptide or mutated form thereof, for example periplasmic proteases such as DegP, DegQ, DegS, Prc (Tsp), and the like.

In an embodiment, the E. coli host cell used in the methods described herein comprises a defective or inactivated gene involved in rhamnose transport. In an embodiment, the E. coli host cell used in the methods described herein comprises a defective or inactivated L-rhamnose-proton symporter (rhaT) gene (UniProt KB accession No. A0A140NH91 for E. coli strain B/BL21-DE3). Inactivation of the rhaT gene may be performed using any method, for example by deleting the entire gene(s) or introducing one or more mutations that prevent the expression of a functional protein (e.g., in the coding region or a promoter/enhancer region). Inactivation of the rhaT gene in combination with inactivation of the rhaB gene may allow for the recombinant protein expression level to be related to the consumption of the inducer L-rhamnose in a concentration-dependent manner. In the case of protein secreted in the periplasm such as CRM197, the expression rate may be adjusted (better controlled) by modifying the L-rhamnose concentration, thereby reducing the aggregation that often occurs when the Sec translocon is saturated, and consequently preventing the formation of inclusion bodies (insoluble CRM197). Shifting the equilibrium from insoluble CRM197 to the more desirable soluble CRM197 may result in a more robust procedure.

In an embodiment, the E. coli host cell used in the methods described herein further comprises one or more modifications for improving the purity of the diphtheria toxin polypeptide produced. For example, it was found by the present inventors using LC-MS/MS analysis that the main contaminating protein band on an SDS-PAGE gel comprises mainly two proteins, namely maltose transporter subunit (malE) and branched-chain amino acid ABC transporter periplasmic binding protein (livK). Accordingly, in an embodiment, the E. coli host cell used in the methods described herein comprises one or more modifications to reduce the levels of malE and/or livK in the purified diphtheria toxin polypeptide preparation. For example, the modification may comprise a genetic alteration to prevent or reduce the expression of the MalE and/or LivK proteins. The entire malE and/or livK genes may be deleted or one or more mutations that prevent the expression of a functional protein may be introduced into the gene (e.g., in the coding region or a promoter/enhancer region). In an embodiment, the genes encoding the contaminant protein(s) (e.g., livK) may be modified such that the protein expressed comprises an affinity tag. Such an approach may be particularly useful for the removal of protein contaminant(s) that are important for cell growth/survival, such as LivK. The term affinity tag as used herein refers to a moiety (e.g. protein, peptide, or molecule) that is recognized by a ligand, such as an antibody, another protein, or a metal ion. Commonly used affinity tags include Calmodulin-tags, E-tags, FLAG-tags, HA-tags, His-tags, Myc-tags, NE-tags, S-tags, SBP-tags, Strep-tags, V5 tags, VSV-tags and biotin-tags. The gene encoding the protein contaminant of interest may be modified to comprise a nucleotide sequence encoding the affinity tag.

In an embodiment, genetic alterations may be introduced into the *E. coli* host cell used in the methods described herein using gene targeting by homologous recombination. As used herein "gene targeting by homologous recombination" refers to genetic engineering techniques that employ homologous recombination to modify DNA sequences in vivo. Such techniques are known in the art and can be used in prokaryotes, such as *E. coli*, to introduce genetic changes into bacterial chromosomes, plasmids, and bacterial artificial chromosomes (BACs). Examples of such techniques are described in Current Protocols in Molecular Biology 1.16.1-1.16.39, April 2014 and Trends in Biotechnology, 2016, 34(7):575-587. Various genetic changes can be introduced using gene targeting by homologous recombination, including gene knockouts, replacements, deletions, insertions, and point mutations.

The efficiency of gene targeting by homologous recombination is low in BL21 *E. coli*, however the present inventors have found that the efficiency of gene targeting in BL21 *E. coli* can be improved by using a BL21 *E. coli* strain that comprises one or more genetic alterations that reduce the level or function of the cell division inhibitor protein SulA, which is part of the SOS checkpoint control system. Without wishing to be bound by theory, the present inventors postulate that it is difficult to carry out gene targeting by homologous recombination in BL21 *E. coli* because BL21 *E. coli* lack the Lon protease.

The SulA protein is a cell division inhibitor in *E. coli* that is induced during the SOS response to DNA alterations such as double-strand breaks. In wild-type *E. coli*, the SulA protein is rapidly degraded by the Lon protease, allowing the cells to resume cell division after double-strand break repair has occurred. In the absence of the Lon protease, the SulA protein persists longer than usual and continues to inhibit cell division. This prolonged inhibition of cell division is believed to reduce the number of *E. coli* cells that can be recovered after gene targeting by homologous recombination in *E. coli* that are void of, i.e. lacking, the Lon protease, such as BL21 strain *E. coli*.

Accordingly, in an embodiment, the *E. coli* host cell used in the methods described herein comprises one or more modifications to reduce the expression or function of the SulA protein in the host cell. For example, the modification may comprise a genetic alteration to prevent or reduce the expression of the SulA protein. The entire sulA gene may be deleted or one or more mutations that prevent the expression of a functional SulA protein may be introduced into the sulA gene (e.g., in the coding region or a promoter/enhancer region). It is expected that reducing or eliminating the function of sulA would improve the efficiency of gene targeting in any *E. coli* strain that lacks the Lon protease. In an embodiment, the host cell comprising one or more modifications to reduce the expression or function of the SulA protein is a BL21 strain *E. coli* host cell, for example a BL21(DE3) strain *E. coli* cell. A further embodiment is an *E. coli* cell lacking a Lon protease, such as a BL21 strain *E. coli* cell, comprising a defective sulA gene. The *E. coli* cell comprising the defective sulA gene may be used to express a heterologous protein of interest, such as but not limited to a Diphtheria toxin polypeptide or a mutated form thereof. Since the *E. coli* cell comprising the defective sulA gene is amenable to gene targeting by homologous recombination, aka gene editing, further mutations or genetic alterations may be introduced into the cell using gene targeting by homologous recombination in order to improve protein expression levels, remove protein contaminants (e.g. MalE and/or LivK), or to confer any other desirable trait to the *E. coli* cell.

Further provided is a method for increasing the amenability of an *E. coli* cell that is void of Lon protease to gene targeting by homologous recombination, the method comprising introducing into the *E. coli* cell a mutation that reduces the function of the sulA gene. As used herein, the amenability of an *E. coli* cell to gene targeting by homologous recombination is considered to be increased by the introduction of a mutation that reduces the function of the sulA gene if the efficiency of gene targeting by homologous recombination in the *E. coli* cell is increased relative to the efficiency of gene targeting by homologous recombination in an *E. coli* cell of the same strain that does not include a mutation that reduces the function of the sulA gene. For example, the efficiency of gene targeting by homologous recombination may be increased by at least 2-fold, at least 3-fold, at least 4-fold, at least 5-fold, at least 10-fold, at least 25-fold, at least 50-fold, at least 100-fold, at least 150-fold, at least 200-fold, at least 250-fold, at least 300-fold, or greater relative to the efficiency of gene targeting by homologous recombination in an *E. coli* cell of the same strain that does not include a mutation that reduces the function of the sulA gene. The efficiency of gene targeting by homologous recombination may be determined by calculating the number of gene edited colony forming units (CFUs) per molar amount of donor substrate DNA. For example, if a single-stranded DNA (ssDNA) oligo is used as a donor substrate, the efficiency of gene targeting by homologous recombination may be calculated as the number of gene edited CFUs/pmol of ssDNA introduced into the *E. coli* cells. Other donor substrate DNAs may be used including, for example, gene targeting vectors and gene targeting PCR fragments. Gene targeting by homologous recombination may be carried out using any suitable technique known in the art, for example using a CRISPR-Cas system.

The construction of appropriate plasmids or expression vectors for expression of diphtheria toxin polypeptide or a mutated form thereof will be apparent to the scientist of ordinary skill in the art. Processes for preparing recombinant heterologous proteins from genetically engineered bacterial host cells such as *E. coli* are well known to those skilled in the art. Recombinant diphtheria toxin polypeptides or mutated forms thereof can be expressed in *E. coli* host cells by any of these methods. Introduction of a nucleic acid into the *E. coli* host cell can be accomplished by any of several standard molecular biology techniques such as those described in Davis et al., Basic Methods in Molecular Biology (1986) and Sambrook et al., Molecular Cloning: A Laboratory Manual, $2^{nd}$ Ed., Cold Spring Harbor Laboratory Press, Cold Spring Harbor, N.Y. (1989) including, without limitation, calcium phosphate transfection, microinjection, electroporation, conjugation, infection and the like. Similarly, any system or vector suitable to maintain, propagate or express polynucleotides and/or express a polypeptide in a host may be used to practice the methods/processes described herein. For example, the appropriate DNA sequence may be inserted into a vector such as a plasmid by standard techniques.

Method/Process for Producing Diphtheria Toxin Polypeptide or Mutated Forms Thereof As noted above, It has been found by the present inventors that significantly improved yields can be obtained by uncoupling biomass growth from recombinant protein induction through the use of a *E. coli* strain defective in rhamnose catabolic pathway (i.e. unable to use rhamnose as a carbon source) and rhamnose as an inducer of protein production. It has also been found that significantly improved yields can be obtained by initiating a "late" induction of protein production, when the optical density (OD) at 600 nm ($OD_{600}$) of the culture is at least about 150, and by performing the protein production step under fedbatch conditions.

Thus, in another aspect, the present disclosure provides a method for producing a Diphtheria toxin polypeptide or a mutated form thereof, the method comprising:
(a) culturing an *Escherichia coli* cell comprising a heterologous nucleic acid construct defined herein in a rhamnose-free culture medium (i.e. a culture medium comprising a carbon source that is not rhamnose) until an optical density at 600 nm ($OD_{600}$) of at least about 150 is reached; and
(b) adding rhamnose to the culture and feeding the culture with a solution comprising a carbon source for a period of time sufficient to produce said Diphtheria toxin polypeptide or mutated form thereof; and
(c) collecting the Diphtheria toxin polypeptide or mutated form thereof produced from the periplasm of said cell.

Thus, in an embodiment, the methods described herein comprise a step (e.g., step (a) above) wherein the *E. coli* host cells are cultured during a growth phase under conditions such that expression of the Diphtheria toxin polypeptide or mutated form thereof is prevented, notably by using a culture medium comprising a carbon source other than the inducer rhamnose. In various embodiments, the culture or fermentation medium may be selected from among rich media, minimal media and mineral salts media. In an embodiment the media is free or substantially free of serum and animal-derived products. Suitable media for production of recombinant polypeptides in *E. coli* are well known in the art. The culture medium may be a defined, semi-defined or complex medium suitable for expression of recombinant proteins in *E. coli*. In an embodiment, the culture medium comprises from about 0.1 g/L to about 100 g/L, about 1 g/L to about 100 g/L, about 2 g/L to about 80 g/L, about 4 g/L to about 60 g/L, about 5 g/L to about 50 g/L, about 5 g/L to about 20 g/L, or about 10 g/L, of a yeast extract. In an embodiment, the culture medium comprises an iron source at a concentration of at least about 0.001 g/L, at least about 0.01 g/L or at least about 0.1 g/L, for example at least about 0.01 g/L to about 1 g/L, about 0.05 g/L to about 0.05 g/L, or about 0.1 g/L to about 0.2 g/L. In an embodiment, the carbon source other than rhamnose is a sugar, e.g. glucose, maltose, lactate and the like; an extract such as peptone, tryptone, yeast extract, etc., or a polyol such as glycerol. In an embodiment, the culture medium further comprises an antifoam agent.

In certain embodiments, expression is performed in bioreactor fermentations. Any scale of fermentation may be employed including 1-liter scale and larger fermentation volumes. In one embodiment, the fermentation volume is or is at least 1 Liter. In other embodiments, the fermentation volume is or is at least 5 Liters, 10 Liters, 15 Liters, 20 Liters, 25 Liters, 50 Liters, 75 Liters, 100 Liters, 200 Liters, 500 Liters, 1,000 Liters, 5,000 Liters, 10,000 Liters, 50,000 Liters, or more.

In embodiments, the length of culture step (a) is at least about 16 hours, at least about 20 hours, at least about 24 hours or at least about 28 hours. In embodiments, the length of culture step (a) is about 20 hours to about 40 hours, about 24 to about 32 hours, about 26 to about 30 hours, or about 28 hours.

In other embodiments, culture step (a) comprises two phases, i.e. a first phase and a second phase. In an embodiment, in the first phase, the culture medium comprises a sugar, for example glucose, as a carbon source, at a concentration of at least about 1 g/L, at least about 2 g/L, at least about 3 g/L, at least about 4 g/L, at least about 5 g/L, at least about 10 g/L, at least about 15 g/L or at least about 20 g/L. In further embodiments, a sugar, for example glucose, is present at a concentration of about 5 g/L or 10 g/L to about 40 g/L or 50 g/L, for example about 10 g/L to about 30 g/L. In an embodiment the sugar is present at a concentration of about 20 g/L. In an embodiment, the length of the first phase of step (a) is at least about 6 hours, at least about 8 hours, at least about 10 hours, or at least about 12 hours. In further embodiments, the length of the first phase of step (a) is about 8 hours to about 16 hours, about 10 hours to about 14 hours, or about 12 hours. In embodiments, the second phase of step (a) comprises feeding the culture with a feed solution comprising a carbon source other than rhamnose, for example glucose. The feeding flow rate may be constant or variable over time. In an embodiment, the feeding flow rate is increased (linearly or exponentially) during the second phase. In an embodiment, the feeding flow rate is at least about 1 mL/L/h, at least about 2 mL/L/h, at least about 3 mL/L/h, at least about 4 mL/L/h or at least about 5 mL/L/h. In an embodiment, the feeding flow rate is about 1 mL/L/h, about 2 mL/L/h, about 3 mL/L/h, about 4 mL/L/h or about 5 mL/L/h to about 30 mL/L/h, about 40 mL/L/h, about 50 mL/L/h, about 60 mL/L/h, about 80 mL/L/h or about 100 mL/L/h, for example about 2 mL/L/h to about 50 mL/L/h, or about 5 mL/L/h to about 40 mL/L/h. In further embodiments, the feeding flow rate at the start of the second phase is about 1 mL/L/h, about 2 mL/L/h, about 3 mL/L/h, about 4 mL/L/h or about 5 mL/L/h and the feeding flow rate at the end of the second phase is about 30 mL/L/h, about 40 mL/L/h, about 50 mL/L/h, about 60 mL/L/h, about 80 mL/L/h or about 100 mL/L/h. In an embodiment, the feeding flow rate at the start of the second phase is about 5 mL/L/h. In an embodiment, the feeding flow rate at the end of the second phase is about 40 L/L/h. In an embodiment, the length of the second phase of step (a) is at least about 6 hours, at least about 8 hours, at least about 10 hours or at least about 12 hours. In further embodiments, the length of the first phase of step (a) is about 8 hours to about 18 hours, about 20 hours, about 22 hours or about 24 hours. In embodiments, the length of the second phase of step (a) is about 10 hours or about 12 hours to about 18 hours or about 20 hours. In an embodiment the length of the second phase of step (a) is about 16 hours. In another embodiment, the feed solution used during the second phase of step (a) comprises a carbon source other than rhamnose, for example glucose, at a concentration of at least about 100 g/L, at least about 200 g/L, at least about 300 g/L or at least about 400 g/L, for example about 200 g/L, about 300 g/L or about 400 g/L to about 700 g/L, about 800 g/L or about 900 g/L. In an embodiment, the carbon source other than rhamnose is at a concentration of about 600 g/L to about 700 g/L, for example about 650 g/L.

When a suitable target culture cell density is reached in step (a), a suitable amount of the inducer, rhamnose, is added to initiate protein production. It has been found by the present inventors that significantly improved yields were obtained by initiating a "late" induction of protein production, when the optical density (OD) at 600 nm ($OD_{600}$) of the culture was at least about 150, for example at least about 180. In embodiments, the $OD_{600}$ of the culture at induction is at least about 160, at least about 170, at least about 180, at least about 190, at least about 200, at least about 210, at least about 220, at least about 230 or at least about 240. In embodiments, the $OD_{600}$ of the culture at induction is between about 150, 160, 170, 180, 190 or 200 to about 220, 230, 240, 250, 260, 270, 280, 290 or 300, for example between about 180 and about 220. In embodiments, the concentration of rhamnose (e.g., L-rhamnose) used for induction is at least about 0.0004% (w/v), at least about 0.005% (w/v), at least about 0.01% (w/v), or at least about 0.1% (w/v). In embodiments, the concentration of rhamnose (e.g., L-rhamnose) used for induction is between about 0.0004% and about 1% (w/v), between about 0.005% and about 0.5% (w/v), between about 0.01% and about 0.2% (w/v), or between about 0.01% and about 1% (w/v), for example about 0.05% (w/v). In an embodiment, the length of step (b) is at least about 2 hours, at least about 3 hours, at least about 4 hours, at least about 5 hours or at least about 6 hours. In a further embodiment the length of step (b) is about 4 hours or about 5 hours to about 7 hours or about 8 hours, for example about 6 hours. In an embodiment, the carbon source present in the feed solution of step (b) comprises or is a carbon source that does not interfere with rhamnose induction, for example glycerol. In another embodiment, the carbon source present in the feed solution of step (b), for example glycerol, is at a concentration of at least about 100 g/L, at least about 200 g/L, at least about 300 g/L or at least about 400 g/L, for example about 200 g/L, about 300 g/L or about 400 g/L to about 700 g/L, about 800 g/L or about 900 g/L. In an embodiment, the carbon source present in the feed solution of step (b) is at a concentration of about 600 g/L to about 700 g/L, for example about 665 g/L. The feeding flow rate in step (b) may be constant or variable over time. In an embodiment, the feeding flow rate in step (b) is constant. In an embodiment, the feeding flow rate in step (b) is at least about 1 mL/L/h, at least about 2 mL/L/h, at least about 3 mL/L/h, at least about 4 mL/L/h or at least about 5 mL/L/h. In an embodiment, the feeding flow rate in step (b) is about 1 mL/L/h, about 2 mL/L/h, about 3 mL/L/h, about 4 mL/L/h or about 5 mL/L/h to about 30 mL/L/h, about 40 mL/L/h, about 50 mL/L/h, about 60 mL/L/h, about 80 mL/L/h or about 100 mL/L/h, for example about 2 mL/L/h to about 30 mL/L/h, or about 5 mL/L/h or 10 mL/L/h to about 20 mL/L/h, for example about 14 mL/L/h.

Growth, culturing and/or fermentation of the *E. coli* host cells is performed within a temperature range permitting survival, and in an embodiment is about 20° C. to about 30° C., about 35° C. or about 40° C., about 22° C. to about 30° C., about 24° C. to about 28° C., about 25° C. to about 27° C., for example about 26° C. In an embodiment, step (a) is performed at a temperature of about 20° C. to about 30° C., about 35° C. or about 40° C., about 22° C. to about 30° C., about 24° C. to about 28° C., about 25° C. to about 27° C., for example about 26° C. In an embodiment, step (b) is performed at a temperature of about 20° C. to about 30° C., about 35° C. or about 40° C., about 22° C. to about 30° C., about 24° C. to about 28° C., about 25° C. to about 27° C., for example about 26° C.

In an embodiment, the process comprises a pre-culture at a temperature of about 37° C. (e.g., for about 8 hours to about 16 hours, about 10 hours to about 14 hours, or about 12 hours) and is followed by growth at the above-noted temperatures prior to and after induction with rhamnose. In other embodiments, culturing comprises growth at about 26° C. prior to and after induction with rhamnose.

In embodiments, the pH of the culture is maintained at about 6.5 to about 7.5, at about 6.5 to about 7.0, or about 6.7 to about 6.9, for example at about 6.8.

It is understood that the cell density at induction, the concentration of inducer, pH and temperature can be varied to determine optimal conditions for expression.

In embodiments, the yield of soluble diphtheria toxin polypeptide or a mutated form thereof obtained per litre of culture is at least about 2.0 g/L, at least about 2.5 g/L, at least about 3.0 g/L, at least about 3.5 g/L, at least about 4.0 g/L, at least about 4.5 g/L, at least about 5 g/L, at least about 5.5 g/L, at least about 6.0 g/L, or at least about 7.0 g/L. In other embodiments, the yield of soluble diphtheria toxin polypeptide obtained is from about 2.0 g/L to about 12.0 g/L, from about 2.0 g/L to about 10.0 g/L, from about 2.0 g/L to about 9.0 g/L, from about 2.0 g/L to about 8.0 g/L, from about 3.0 g/L to about 10.0 g/L, from about 3.0 g/L to about 9.0 g/L, from about 3.0 g/L to about 8.0 g/L, from about 4.0 g/L to about 10.0 g/L, from about 4.0 g/L to about 9.0 g/L, from about 4.0 g/L to about 8.0 g/L, from about 5.0 g/L to about 10.0 g/L, from about 5.0 g/L to about 9.0 g/L, from about 5.0 g/L to about 8.0 g/L, or from about 5.0 g/L to about 7.0 g/L. As used herein, the "yield of soluble diphtheria toxin polypeptide or a mutated form thereof" is intended to refer to the yield of diphtheria toxin polypeptide or a mutated form thereof that is produced by the *E. coli* in soluble form. The "yield of soluble diphtheria toxin polypeptide or a mutated form thereof" is not intended to include protein that is produced by the *E. coli* in insoluble form and subsequently subjected to a solubilisation treatment, for example treatment with a solubilizing agent such as guanidine hydrochloride, urea, or sarkosyl, to convert the protein to soluble form.

Diphtheria toxin polypeptides or mutated forms thereof may be purified by methods known in the art, see for example the processes described in WO2011/123139; U.S. Pat. No. 6,689,871 and Rappuoli et al., *Journal of Chromatography*, 268, 1983, pp 543-548. In an embodiment, the purification comprises ion-exchange chromatography and/or hydrophobic interaction chromatography and/or mixed-mode chromatography. In an embodiment, the purification comprises an affinity chromatography. Affinity chromatography may be particularly useful to remove protein contaminants from the preparation that were modified to include an affinity tag, as described above. An example of affinity chromatography is immobilized metal affinity chromatography (IMAC) that binds to proteins comprising a His-tag, or affinity chromatograph with a resin comprising avidin or streptavidin that binds to proteins comprising a biotin tag.

Methods to characterize yield, purity, stability, nicking degree, toxicity, endotoxin content are well established and define the quality for use of diphtheria toxin polypeptide or mutated form thereof in a vaccine. Analysis of diphtheria toxin polypeptide or mutated form thereof may be done by, e.g., high performance size exclusion chromatography, isoelectric focusing, ELISA, Bradford assay, SDS-PAGE and Western Blot, molecular weight determination by mass spectroscopy, N-terminal sequencing, amino acid analysis, reverse phase liquid chromatography, electrospray mass spectroscopy, and peptide mapping by mass spectroscopy after tryptic digestion.

EXAMPLES

The present invention is illustrated in further detail by the following non-limiting examples.

Example 1: Assessment of Different Periplasm Secretion Signal Peptides

Different periplasm secretion signal peptides were compared. The following signal sequences were tested in flasks: MglB, TorT, OmpC, OmpT (mutated form), OmpTR (the original form of OmpT), OmpTCH (mutated form of OmpT, more hydrophobic), OmpTCinv (another mutated form of OmpT), OmpA, OmpF, LamB, PIII, Sufl, TorA, SfmC, Azu, Ibp, 1834. The following signal sequences were tested in fermentors: Azu, Ibp, 1834, OmpT (mutated form), OmpTR, OmpTCinv, OmpC, OmpF.

Figure 3B:
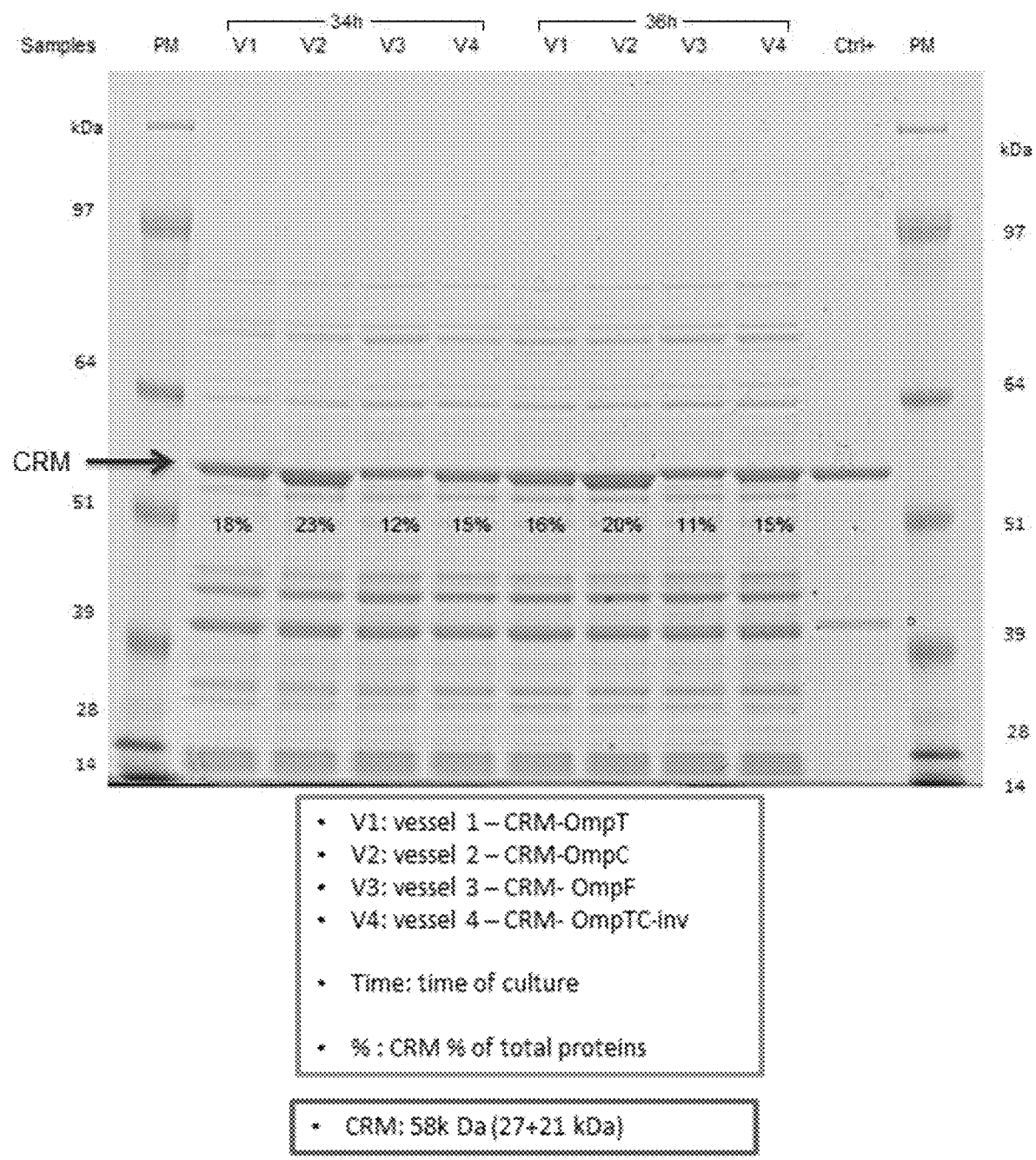
Figure 3C:
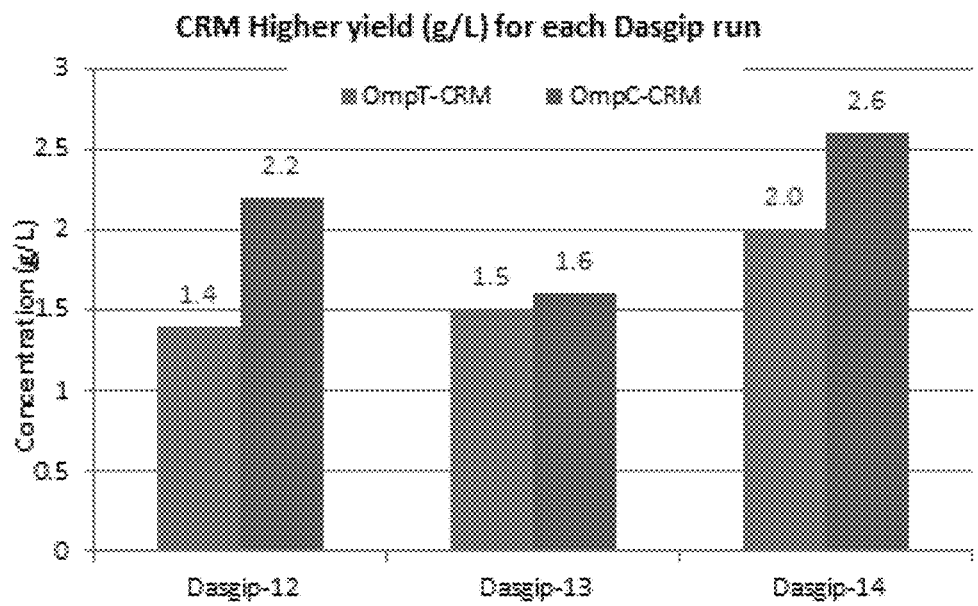

Further tests were performed in flasks using different signal sequences using CRM197 constructs under the control of a rhamnose-inducible promoter. The results are presented in FIG. 3A. OmpC, OmpT (mutated form), OmpTR and OmpTCH gave similar results in flasks, and were then assessed in reactors. As shown in FIGS. 3B and 3C, better production was achieved using the OmpC signal sequence.

Example 2: Carbon Source During Feed

Figure 4A:
Figure 4B:
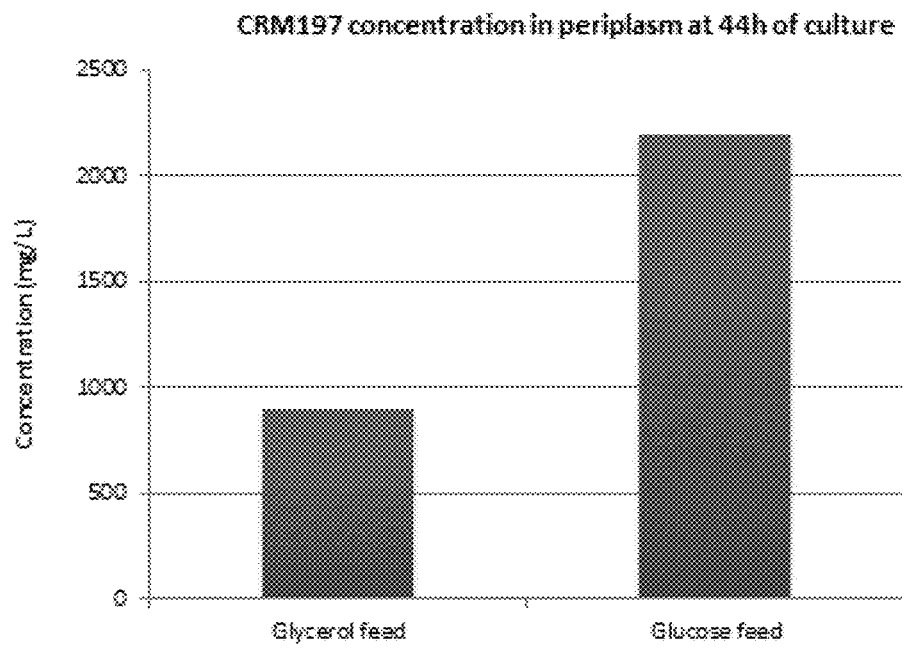

Feeding solutions comprising two different sources of carbon (glucose and glycerol) were compared using a CRM197 construct comprising an OmpT signal sequence (mutated form) under the control of a rhamnose-inducible promoter. A punctual addition of rhamnose was used to induce the culture. The carbon source concentrations were adjusted so that the same molar quantity of carbon was delivered by the feed. There was not a great difference between glucose and glycerol in terms of growth (FIG. 4A), but the yield was much higher (about 2- to 3-fold) for a 44 h culture grown on glucose (FIG. 4B).

Example 3: Timing of Induction

Figure 5A:
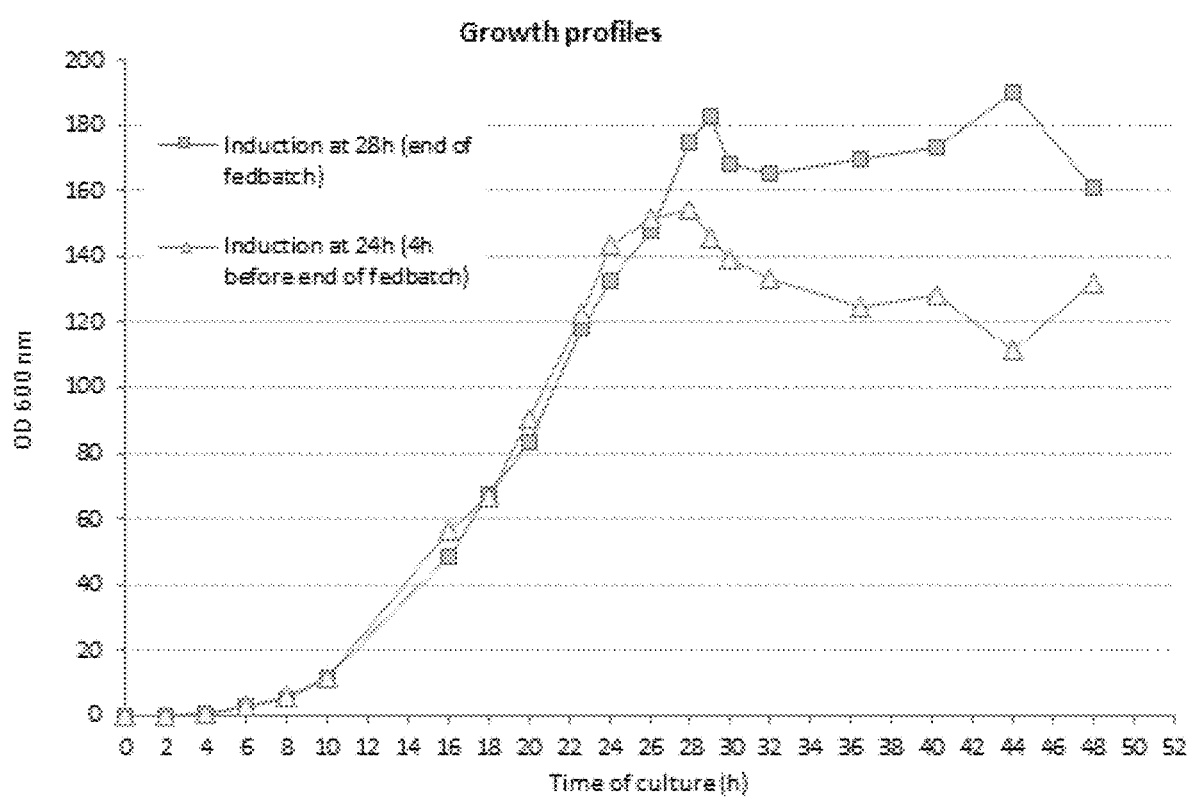
Figure 5B:
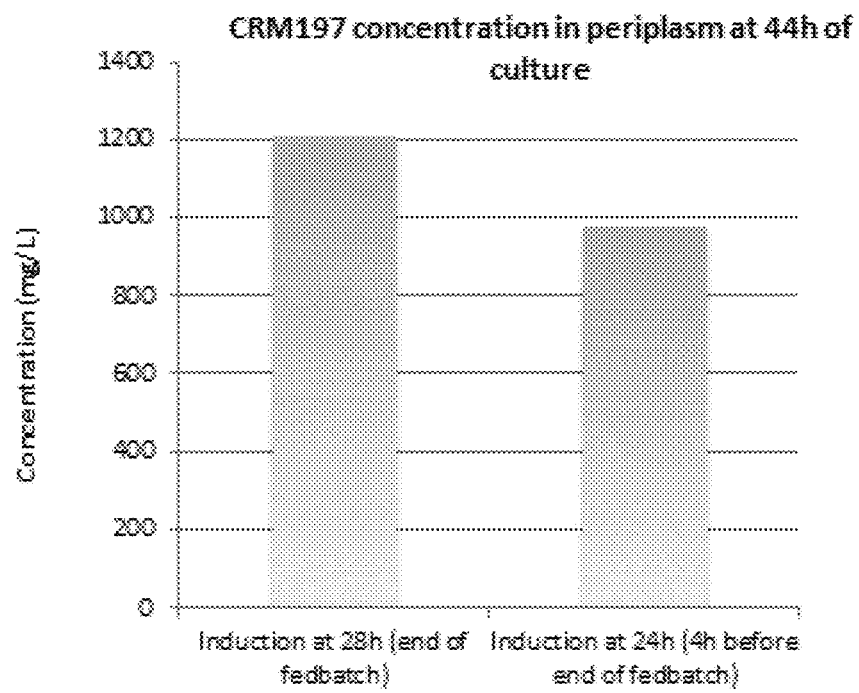

With the use of glucose in the batch phase (see FIG. 4B), production can only occur when glucose is depleted because of catabolic repression of glucose. Induction of expression could be carried out during the fedbatch phase (at 24 h) because glucose is limiting during this phase, but tests performed showed that a later induction (28 h) was more efficient (higher biomass, higher production), as shown in FIGS. 5A and 5B. Induction seems to stop the growth, so uncoupling growth and production using a late induction leads to higher yields. These tests were done using a CRM197 construct comprising an OmpT signal sequence (mutated form) under the control of a rhamnose-inducible promoter.

Example 4: Post-Induction Feed

Figure 6A:
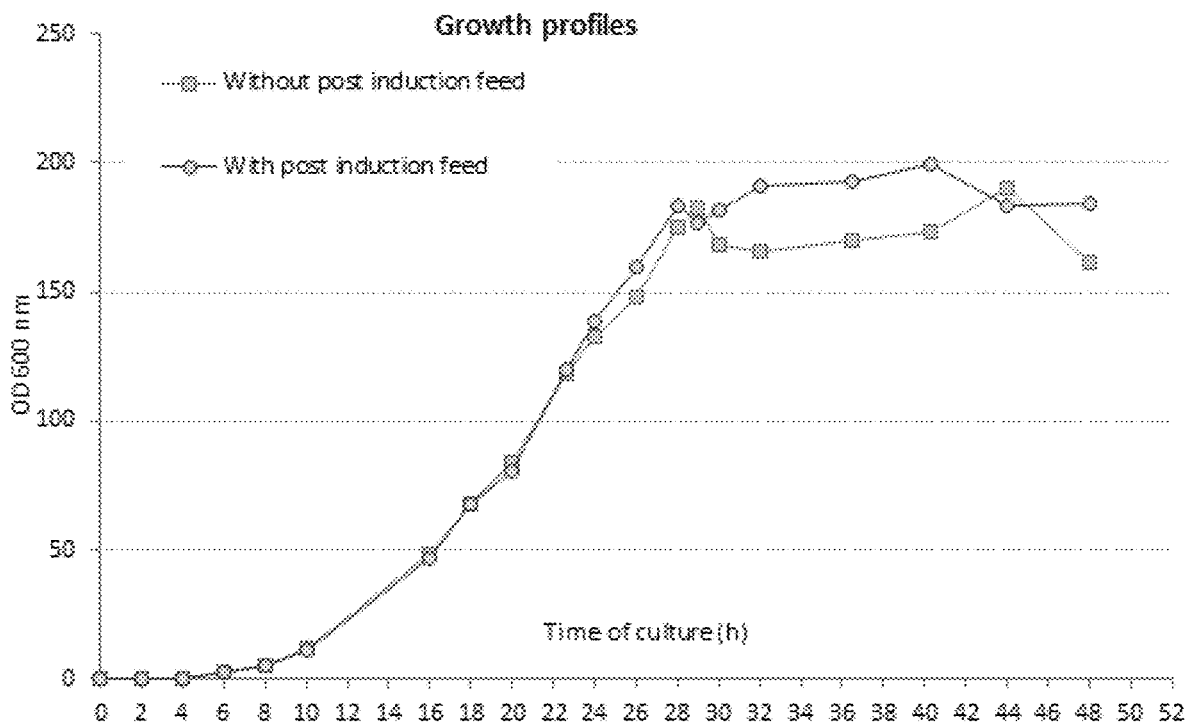
Figure 6B:
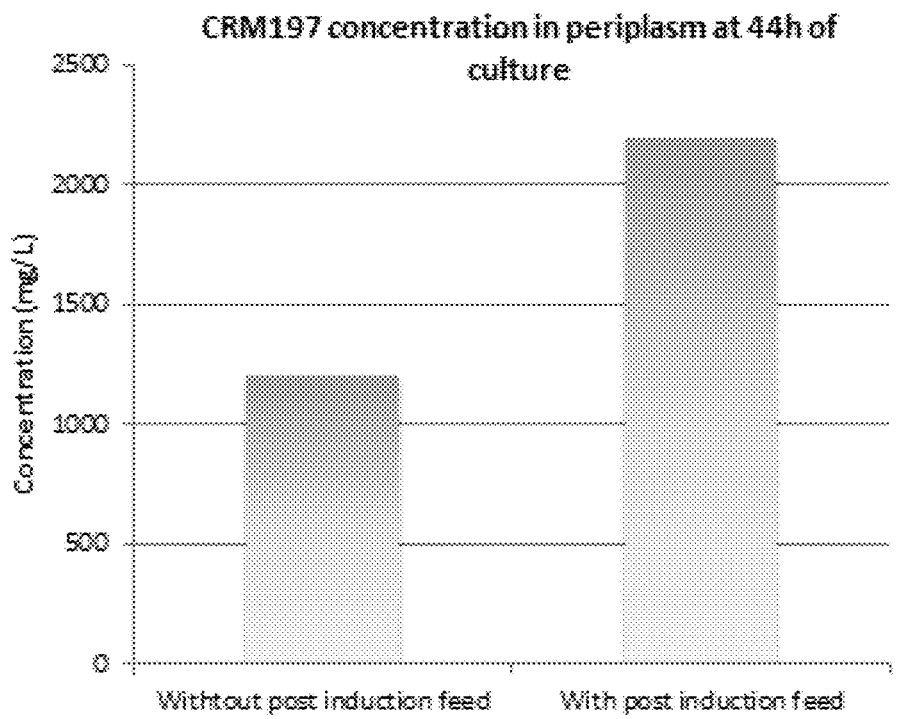

It was next tested whether the addition of a second feed after induction improves production. Glycerol was chosen to avoid the negative retro-control of glucose on the rhamnose promotor, and the feed rate (14 mL/h per liter of starting volume) was adjusted to meet the needs of the bacteria while limiting by-product formation (acetate). The results presented in FIGS. 6A and 6B show that the use of a post-induction feed with glycerol increases both biomass and protein yield. These tests were done using a CRM197 construct comprising an OmpT signal sequence (mutated form) under the control of a rhamnose-inducible promoter.

Example 5: Conditions for Induction

Figure 7:
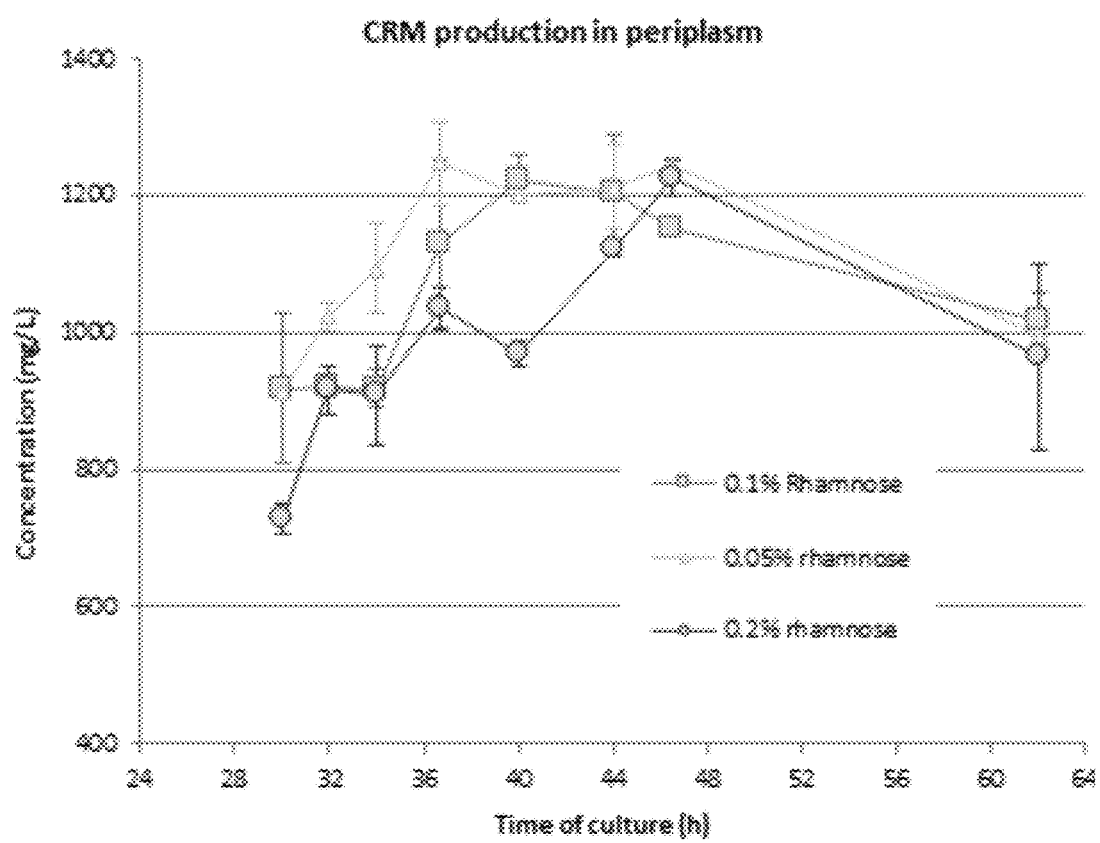
Figure 8:
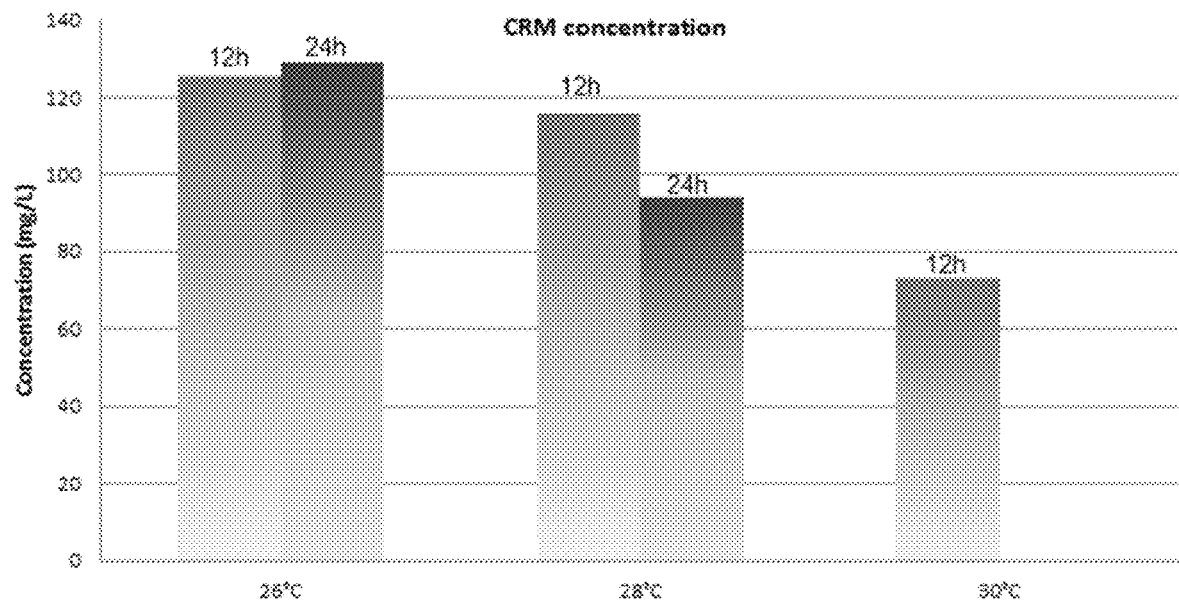

Various concentrations (0.05%, 0.1% and 0.2%) of rhamnose were then tested in Dasgip reactors (2.2 L) using a punctual addition at 28 h of culture. Good yields were obtained at all concentrations, with 0.05% leading to slightly higher production. Other tests in micro-reactors at different temperatures (26° C., 28° C. or 30° C.) using a punctual addition of 0.1% L-rhamnose showed that a temperature of 26° C. gave better protein yields after 12 h (left bars) or 24 h (right bars) (FIG. 7).

Example 6: Optimized Process for Producing CRM197

1—Bacterial Strains and Constructs

The bacterial strain used was *Escherichia coli* BL21 ΔrhaB with plasmid pD861-OmpC-CRM197, with the *E. coli* optimized CRM197 gene being under the control of rhaP$_{BAD}$ promoter, and having kanamycin resistance. A nucleotide sequence encoding the OmpC signal sequence (MKVKVLSLLVPALLVAGAANA, SEQ ID NO:1) was added at the 5' end of the optimized CRM197 gene sequence allowing CRM197 production in the periplasm of the cells. The amino acid and nucleotide sequences of the OmpC-CRM197 construct are depicted in FIGS. 2A and 2B, respectively.

The rhamnose gene, encoding for the second enzyme allowing the catabolism of the rhamnose, L-rhamnulose kinase (rhaB), was mutated (inactivated) by inserting two nucleotides at position 221 of the gene, creating a detrimental frameshift in the sequence (FIG. 11, SEQ ID NO:8).

This mutation prevents the utilization of rhamnose as a carbon source by the cells.

2—Media and Solutions a) Preculture:

SB or LB medium+50 mg/L kanamycin b) Fermentation Medium RIE+

The recipe of the fermentation medium was based on the medium described in Riesenberg (High cell density cultivation of *Escherichia coli* at controlled specific growth rate. *J Biotechnol.* 1991 August; 20(1):17-27), with some changes. The medium was enriched with 10 g/L of yeast extract to make a semi-synthetic version to allow for high cell density fermentation, and the iron concentration has been increased. L-rhamnose monohydrate was used as the inducer, and the antibiotic kanamycin sulfate was added to the medium.

c) Feed Solution for Growth

The feed solution used was different than that disclosed in Riesenberg (supra). A glucose-based feed (650 g/L of glucose) was used during the fedbatch period to increase biomass. The feed solution for growth also comprised (NH$_4$)$_2$SO$_4$, NH$_4$Cl and MgSO$_4$-7H$_2$O.

d) Feed Solution for Post-Induction

A feed-based carbon source (glycerol at 665 g/L) was used during the post-induction fedbatch period to avoid carbon limitation during production. The feed solution post-induction also comprised (NH$_4$)$_2$SO$_4$, NH$_4$Cl and MgSO$_4$-7H$_2$O e) Other Solutions/Reagents Used Acid: phosphoric acid 5M Base: Ammonium hydroxide 28-30%

Antifoam: Antifoam 204 ⅓ (Sigma-Aldrich®)

3—Preculture

The preculture was prepared by inoculating a 250-mL flask containing 25 mL of LB or SB medium+50 mg/L of kanamycin with a loopful of material scratched from the BL21ΔrhaB/pD861-OmpC-CRM197 frozen culture. The incubation was done for 12 h at 37° C., with shaking at 250 rpm. The next day, purity was checked by wet mount observation. The 2.2 L reactor containing 1.0 L of RIE$^+$ medium was inoculated with a volume calculated to reach an initial OD at $600_{nm}$ of about 0.1.

4—Fermentation

The fermentation process was divided into two stages. The first stage of the culture was directed toward growth to produce biomass, and included a batch phase on glucose and a fedbatch phase with a linear feed rate (also on glucose) until the biomass reached a maximum. The second stage was then implemented and was directed toward recombinant CRM197 production rather than growth. It included the end of the glucose feed, the induction with rhamnose addition and the set-up of a constant post-induction feed, on glycerol.

Each glass fermentation vessel (Dasgip® fermentors from Eppendorf® were used) containing 1 L of RIE$^+$ medium (no rhamnose added at this point), 20 g/L glucose+kanamycin (50 mg/L) was inoculated with a 12 h culture to reach a starting value of $OD_{600\ nm}$=0.1. The feed was initiated when the $pO_2$ peak appeared (typically > to 60%, which indicates glucose depletion), about after 12 h of culture. The feed flow rate was then started at 5 mL/h and increased to 40 mL/h over a 16 h period. This feed rate was determined in order to target a low growth rate with no or minimal glucose accumulation in the medium. This feeding strategy also avoided the production of by-products like acetate (which is harmful for both the growth and the production) that the strain usually produces.

Figure 9:
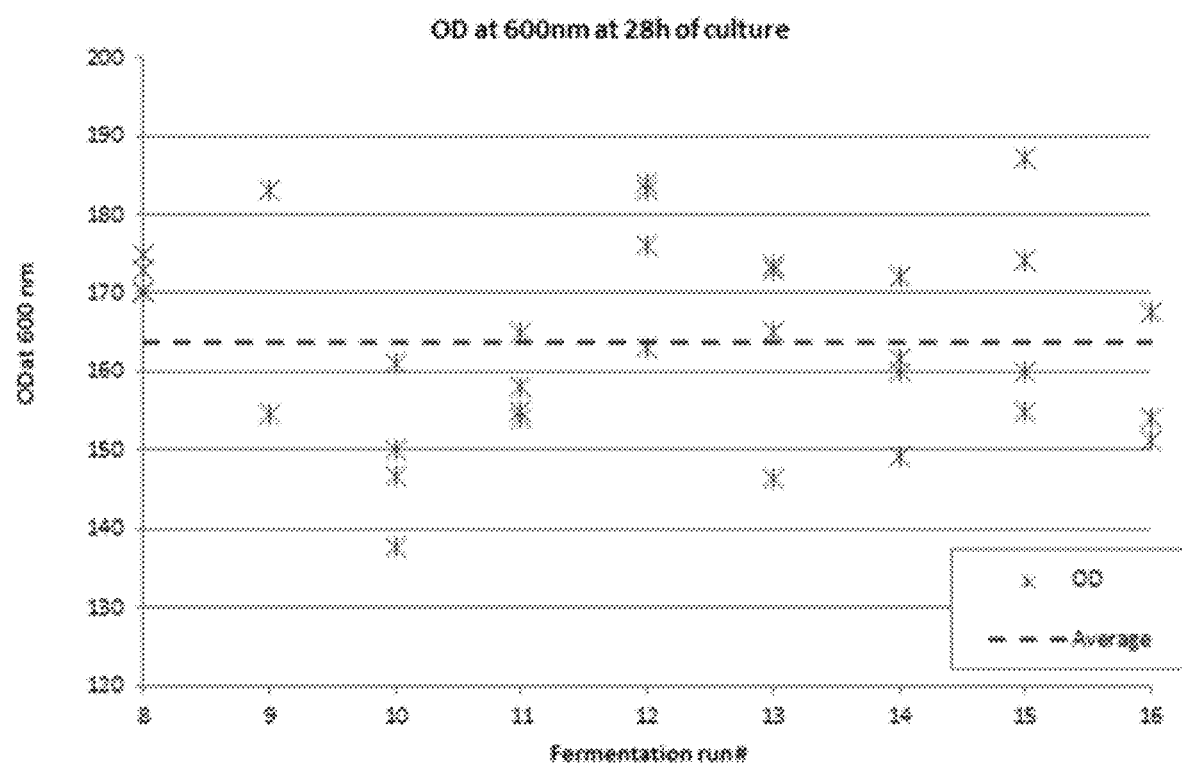

When the glucose feed ended, the cells were induced with 0.05% (w/v) L-rhamnose at 28 h of culture (at that time, the $OD_{600nm}$ was typically between 140 and 190, with an average of about 164—see FIG. 9). The post-induction feed (feed rate of 14 mL/h) was immediately started for a period of 6 h, and the protein was collected (34 h of culture was determined to be the best time to harvest with the highest yield). The feed rate utilized was also assessed for its ability to avoid glycerol accumulation and production of by-products. The vessel was sampled regularly for $OD_{600\ nm}$, pH, organic acids and protein dosage (total protein and recombinant protein).

The culture in a 2.2 L Dasgip® reactor was incubated at 26° C., which was determined to give better results relative to the other temperatures tested (37° C., 30° C. and 28° C.). A lower temperature allows the correct folding of the protein and is believed to minimize proteolytic activity. The pH was maintained at 6.80±0.05 using phosphoric acid 5M and ammonium hydroxide 28-30%. The foam was controlled by Mazu® antifoam (antifoam 204) addition (using a probe sensitive to foam). The $pO_2$ was maintained at 30% saturation by agitation, within the 200-1200 rpm range, aeration, within the 1-4 VVM (gas volume flow per unit of liquid volume per minute) and 02 enrichment within 21-100%.

5—Cell Lysis and Periplasmic Fraction Separation

Figure 10A:
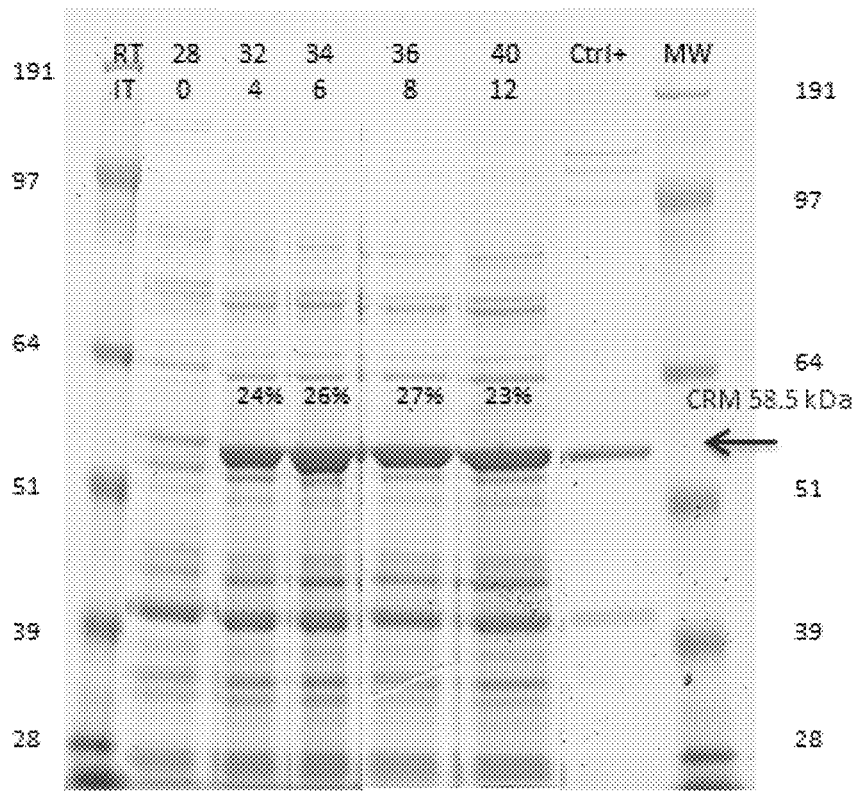
Figure 10B:
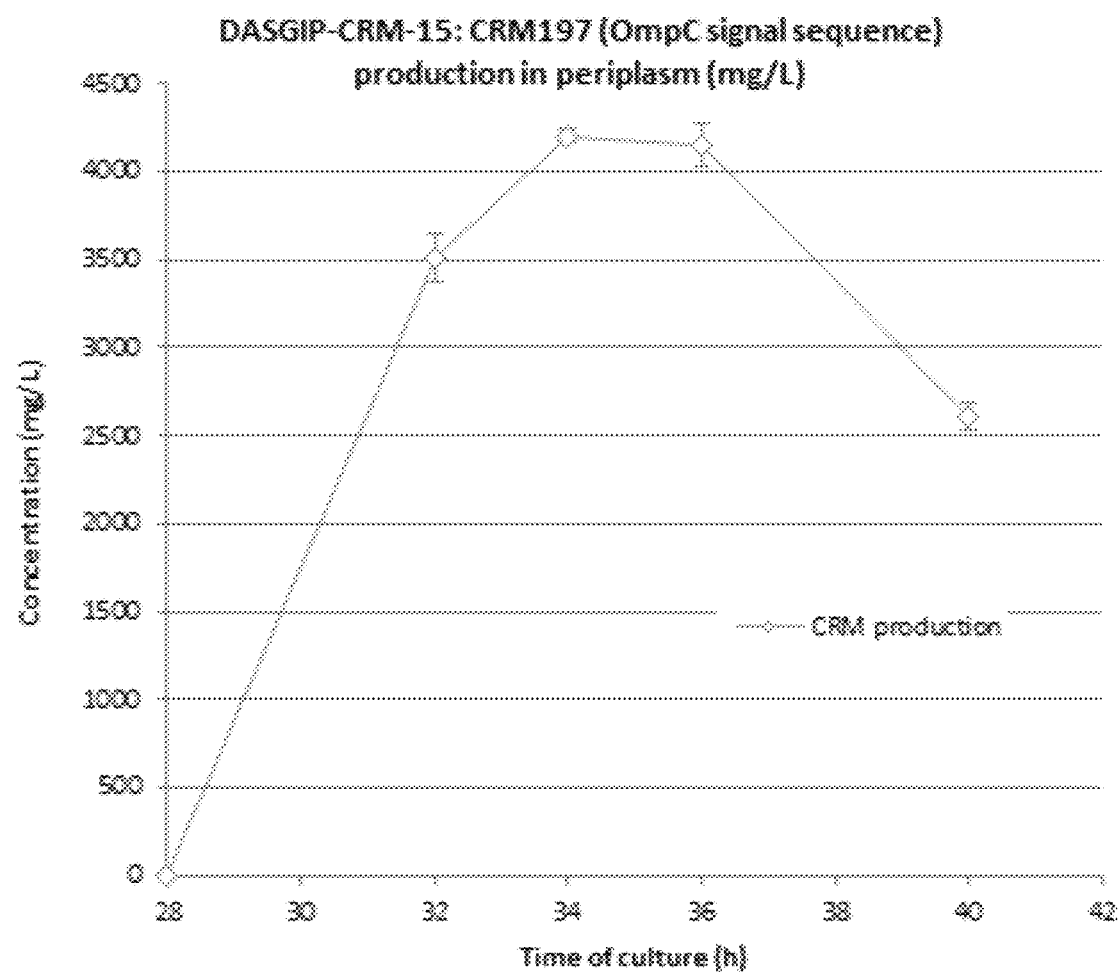

The CRM197 protein was produced in the periplasm of the cell. A harvested cell pellet corresponding to 3 $OD600_{nm}$ of culture was resuspended in 1 mL of cold TES solution (0.5 M sucrose, 0.2 M Tris pH 8.0, 0.5 mM EDTA), incubated 5 minutes at 4° C. with gentle agitation and centrifuged at 13,000 rpm for 3 minutes. The supernatant was discarded; the pellet was resuspended with 0.5 mL cold MilliQ® water, incubated 15 minutes at 4° C. with gentle agitation and then centrifuged at 13,000 rpm for 3 minutes. The supernatant represents the periplasmic fraction. An SDS-PAGE gel (Bolt 8% Bis-Tris, MOPS buffer) was run to confirm CRM197 production. The density of the corresponding gel band size (CRM197=58 kDa in size) was evaluated (FIG. 10A) and the concentration of the total proteins was determined using a Bradford assay (FIG. 10B). These results show that periplasmic yields of up to more than 4 g/L can be obtained using this optimized process.

Example 7: Identification of Main Protein Contaminants in Purified CRM197 Preparations The purification process of CRM197 from the periplasm extraction involved three steps, an anion-exchange column, a hydrophobic column and a mixed-mode column. At the end of the process, it was determined that CRM197 was pure at 97-98%. One contaminating band was slightly visible on SDS-PAGE gel at ~40 kDa. The contaminating band seen after the first purification step (FIG. 12) was extracted from the gel and analysed by liquid chromatography tandem-mass spectrometry (LC-MS/MS). The sequenced peptides matched two *E. coli* proteins, a maltose transporter subunit (MalE) and a branched-chain amino acid ABC transporter periplasmic binding protein (LivK). Removal of either or both these proteins from the preparations would lead to a purer CRM197.

Example 8: Use of a sulA Knockout to Improve the Efficiency of Gene Editing by Homologous Recombination in BL21

Overview

Gene editing by homologous recombination is difficult in BL21 *E. coli*. The present inventors have illustrated by attempted gene editing of a LacZ reporter in BL21 using the CRISPR-lambda RED system as described in Zhao, D. et al., *Microbial Cell Factories*. 15: 205 (2016) and in Li, Y. et al. *Metabolic Engineering*. 31: 13-21 (2015). Recombination efficiency was very low, however some lacZ mutants were obtained. After verifying the presence of the correct mutation, one clone was subjected to whole genome sequencing to identify any off-target mutations. A frame-shift mutation in the sulA gene was identified.

SulA is a highly unstable protein that stops cell division when the SOS response is activated by double-stranded DNA breaks (Ishii, Y and Amano, F., *Biochem J.* 358: 473-80 (2001)). Once DNA repair is complete, SulA is quickly removed by the Lon protease. However, this protease is absent in BL21 *E. coli*, allowing SulA to persist and impede cell division far longer than it would in an *E. coli* strain comprising the Lon protease.

To determine whether sulA mutations were present in any of the other lacZ mutants generated by CRISPR-lambda RED gene targeting, the sulA gene was then sequenced in seven of the clones obtained. All seven clones possessed a mutation in the promoter/operator region of sulA or a mutation disrupting the sulA coding sequence.

1—Targeting lacZ Using the CRISPR-Lambda RED Gene Targeting System

A plasmid producing a guide RNA targeting the lacZ gene was created by PCR and Golden Gate Assembly method using the pGRB plasmid as a template (Addgene #71539). The resulting plasmid (pGRB-lacZ) will express the gRNA using a very strong synthetic promoter.

Figure 16:
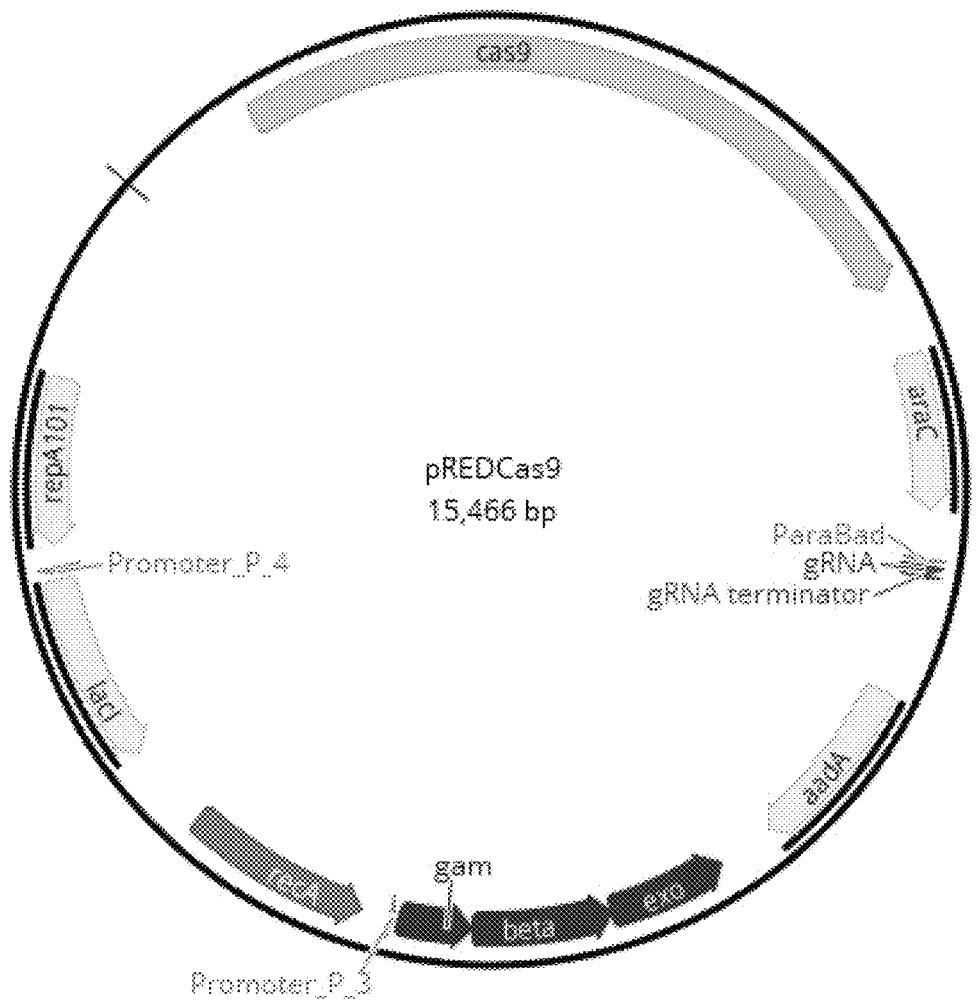
FIG. 16 depicts a map of the pREDCas9 plasmid.

In parallel, the plasmid pREDCas9 (FIG. 16), containing the *Streptococcus pyogenes* Cas9 gene as well as the λ-RED recombinase genes and an extra copy of recA was transformed into W3110 (used as a K-12 control strain) and BL21 strains. Competent cells prepared for these strains bearing pREDCas9 were prepared following a standard protocol, but in the presence (or absence) of IPTG to induce λ-RED recombinase gene expression.

The competent cells were than electroporated in the presence of 0.1 nmol of ssDNA and 100 ng of the prepared pGRB-lacZ plasmid. The ssDNA consisted of an oligo comprising the 9 nucleotides to be changed (creating 2 stop codons) flanked by 40 homologous nucleotides on either side. To prevent nuclease digestion of the oligo, the four first nucleotides had a phosphorothiate linkage instead of a phosphodiester linkage, which substitutes a sulfur atom for a non-bridging oxygen in the phosphate backbone. After 3 or 24 hours of recovery at 30° C., the cells were plated on agar plates containing spectinomycin, ampicillin and X-gal, and incubated at 30° C. for up to 48 hours.

To confirm the effectiveness of the knockout method, first the K-12 W3110 strain was used for knockout of the lacZ gene. Using a recovery time of 3 hours after electroporation, and after 24 hours incubation on the agar plate, >900 CFUs/pmol of ssDNA were obtained (all white colonies, with the exception of 2 blue colonies). Five W3110 clones were sequenced and all had the expected mutation in the lacZ gene.

Figure 17:
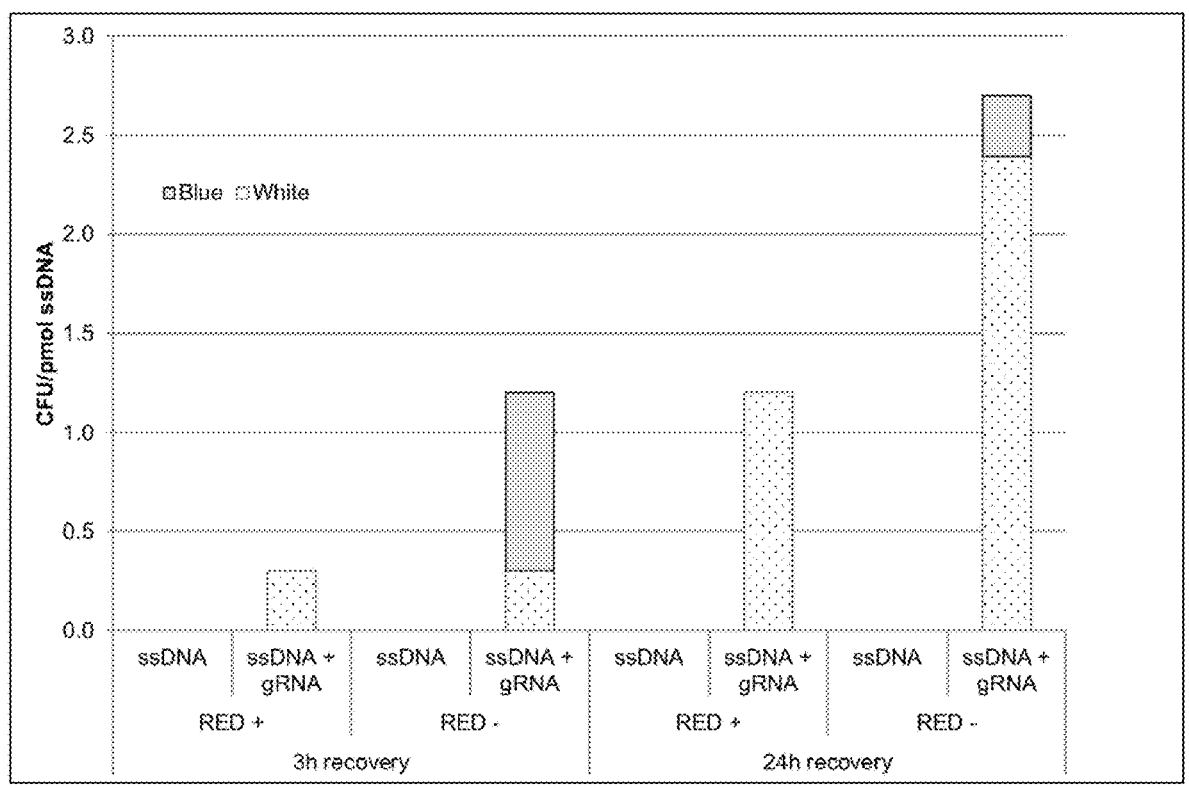
FIG. 17 is a graph showing the number of CFUs obtained after gene targeting of lacZ using CRISPR-lambda RED in a BL21 *E. coli* strain, allowing the cells 3 hours or 24 hours of recovery after electroporation.

The same experiment was then carried out using a BL21 strain. As shown in FIG. 17, the standard homologous recombination protocol using an ssDNA as donor DNA, in the presence or absence of λ-RED recombinases, did not produce any clones. The sequence of the ssDNA is provided as SEQ ID NO: 9. However, when the plasmid pGRB-lacZ, which expresses the gRNA targeting lacZ, was present a few colonies were obtained (<3 CFUs/pmol of ssDNA). These colonies appeared only after 48 hours of incubation on the agar plate and the colonies were unusually small.

A 500 bp region surrounding the expected mutation in the lacZ gene was amplified and sequenced. When the phage recombinase genes were expressed, all of the BL21 clones showed the mutation introduced by the ssDNA, while in the absence of phage recombinase expression only 2 out of 5 clones included the expected mutation.

The genome of one of the BL21Δ/acZ mutant clones created by the CRISPR-lambda RED method was fully sequenced to detect any off-target mutations. Only two discrepancies were observed in the mutant genome when it was compared to the genome of the parental strain (BL21). First, a deletion between mcrB and the mobile element insB-30 had completely removed the gene symE. The product of this gene is part of a toxin-antitoxin system regulated by the SOS response.

When the genomic DNA of the bacteria is damaged, by Cas9 in this case, the SOS response represses the transcription of SymR RNA, a non-coding RNA that inhibits the translation of SymE. The toxin SymE will repress the transcription within the cell and will cleave all mRNA until the genomic DNA is repaired. This deletion was detected in 2 out of 7 mutants tested.

Mutations were also identified in the sulA gene (or its promoter/regulatory region) in all 7 of the clones tested. A summary of the sulA mutations identified is provided in Table 1.

TABLE 1

Mutations identified in the sulA locus in BL21ΔlacZ mutant clones.

| Clone # | Sequencing result |
|---|---|
| 21 | T→C 42 bp upstream of start codon |
| 22 | A missing at position 80, creates frameshift |
| 23 | T→C 42 bp upstream of start codon |
| 24 | A missing at position 80, creates frameshift |
| 27 | G→A at position 198, changes Trp to STOP |
| 31 | G→A at position 198, changes Trp to STOP |
| 34 | A→G 18 bp upstream of start codon |

Figure 18:
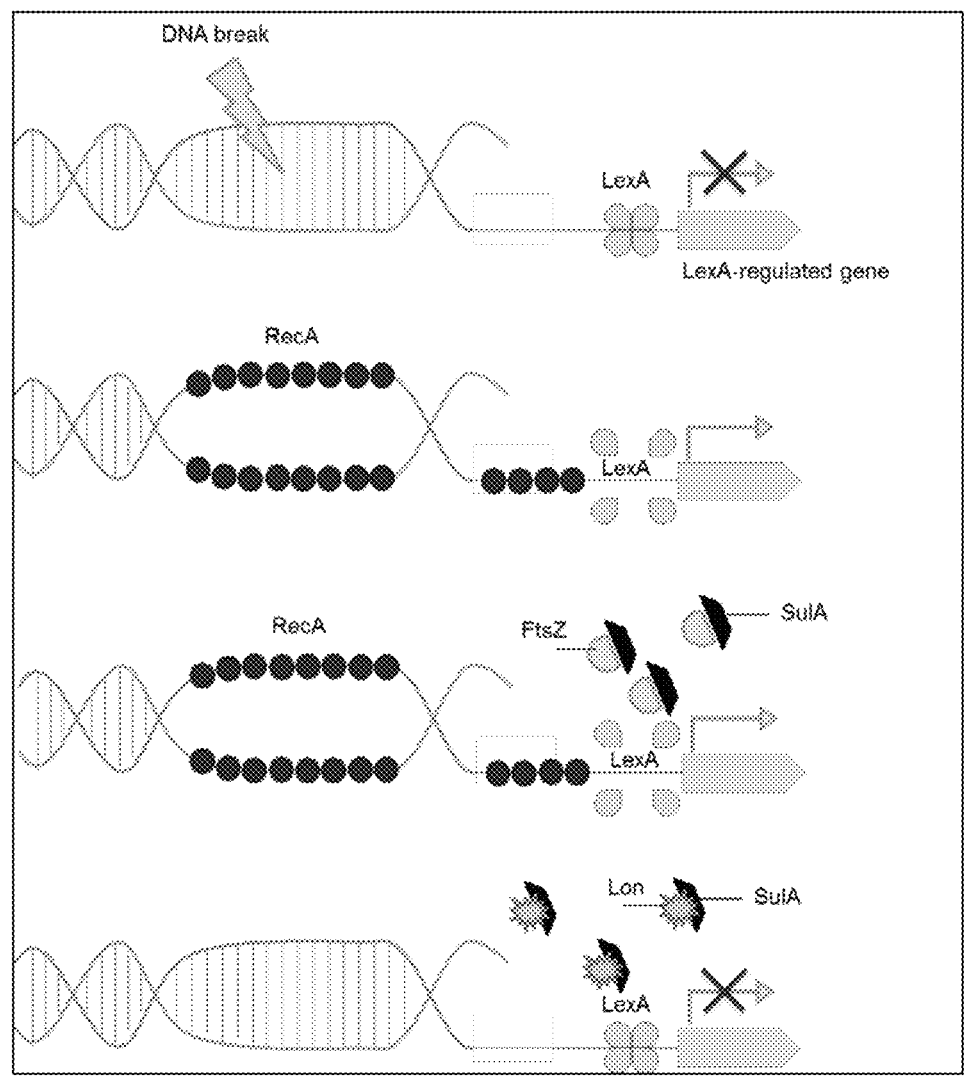
FIG. 18 is a schematic depicting the SOS response in *E. coli*.

As shown in FIG. 18, SulA will bind to FtsZ, inhibiting cell division in order to give the cell time to repair its genomic DNA in response to a double-strand break. Once the DNA repair is complete, SulA is quickly removed by the Lon protease, but for the BL21 strain, which doesn't express Lon, SulA inhibits cell division for a longer period of time.

Part of the SOS response is the transcription of DNA polymerases of low fidelity, which create mutations in the genome such as the sulA mutations we have observed. The present inventors believe that these sulA mutations allow the cells to divide so growth can restart, resulting in the few colonies observed after 48 hours of recovery.

2—Testing the Effect of a sulA Mutation on the Efficiency of CRISPR-Cas9 Gene Editing in BL21

To confirm that the SOS response caused by the DNA damage from Cas9, in association with the absence of the Lon protease, was responsible for the low recombination efficiency in BL21, we repeated the lacZ knockout in a BL21ΔsulA mutant using the method described above.

As shown in FIG. 19, the recombination efficiency increased approximately 300-fold when the CRISPR-lambda RED method was used in a BL21 sulA knockout strain (~375 CFUs/pmol of ssDNA) compared to the previous experiment using the BL21 strain with a wild-type sulA gene (<3CFUs/pmol of ssDNA). All of the white clones tested (10/10) showed the expected lacZ mutation.

Further experiments have been carried out using CRISPR-Cas9 to target other genes in a BL21 ΔsulA background. Using this background, the inventors have been successfully able to knock out degP, elaD, rhaT, and malE; introduce precise mutations into an essential gene (secY), and duplicate genes in the genome (dsbA, dsbC).

Example 9: Removal of Main Protein Contaminants in Purified CRM197 Preparations

As described in Example 8, the presence of a sulA mutation in BL21 greatly increases the efficiency of gene editing by CRISPR-Cas9. The inventors wished to target malE and livK by gene editing to remove the MalE and LivK protein contaminants from the CRM197 protein preparation. Therefore, to improve the efficiency of the gene targeting process, ΔsulA was included in the background and these genes were targeted in a BL21 ΔrhaB ΔsulA strain. The sequence of the sulA mutation employed is depicted in FIG. 20 (SEQ ID NO:10).

To determine whether MalE was the major ~40 kDa contaminant of CRM197 preparations, a malE knockout strain was created by CRISPR/lambda RED method using pREDCas9 and pGRB plasmids (Zhao et al., Microbial Cell Factories. 15: 205 (2016); Li, Y. et al. Metabolic Engineering. 31: 13-21 (2015)). A ssDNA targeting the beginning of malE gene was used to change nucleotides 79-86 and create an insertion of 3 stop codons. After verification of the expected mutation by sequencing and removal of the CRISPR plasmids, the CRM197 expressing plasmid was inserted in the resulting strain (B0023=BL21 ΔrhaB ΔsulA ΔmalE). An autoinduction protocol was used to express CRM197 from the mutant strain. Briefly, 0.1% (w/v) L-rhamnose and 0.05% (w/v) glucose were added to 25 mL of LB medium and inoculated with a preculture of B0023/ pD861-OmpC-CRM197. The flask was incubated at 26° C. for 5 hours. The periplasmic proteins from 20 mL of culture were extracted via osmotic shock, applied on an anion-exchange column and visualized on SDS-PAGE gel. In parallel, the same process was applied to the BL21 ΔrhaB clone expressing CRM197. The contaminating ~40 kDa was still visible in the ΔmalE mutant, providing evidence that the main ~40 kDa protein contaminant is LivK.

LivK is an amino-acid transporter, which if deleted might affect the fitness of the cell. In order to easily remove the contaminating protein from the CRM197 preparation, an affinity tag such as a histidine tag (His tag) will be added to the C-terminus of the protein using the same CRISPR/ lambda RED method described for the knockout of malE. The mutation will be done in the B0023 strain (BL21 ΔrhaB ΔsulA ΔmalE). To test the efficiency of the method, a culture will be auto-induced as described above and the periplasmic protein extraction will first be run through an immobilized metal affinity chromatography (IMAC) column that binds the His tag, then applied to an anion-exchange column. The elution fractions will be visualized on SDS-PAGE gel to observe the reduction or disappearance of the contaminating protein.

Example 10: Preparation of a Rhamnose Transporter-Deficient *E. coli* Strain

The system used to produce CRM197 in *E. coli* described herein relies on rhamnose induction. To avoid cells consuming the inducer, the second enzyme in the L-rhamnose utilization pathway (rhaB) was deleted, allowing the cell to express CRM197 using a fixed amount of the inducer. In an effort to improve the tunability of expression, a rhamnose transporter (rhaT) mutation was further introduced in addition to the rhaB deletion. In *E. coli* lacking both rhaB and rhaT, the expression rate of recombinant proteins can be regulated in an L-rhamnose concentration-dependent manner (Hjelm, A. et al. *ACS Synthetic Biology.* 6: 985-994 (2017)). In the case of a protein secreted into the periplasm, as for CRM197, decreasing the L-rhamnose concentration and thus decreasing the expression rate, could reduce the aggregation that often occurs when the Sec translocon, the pore in the membrane through which CRM197 passes to enter the periplasmic space, is saturated. Consequently decreasing the expression rate may prevent the formation of inclusion bodies (insoluble CRM197). Shifting the equilibrium from insoluble CRM197 to soluble CRM197 results in a more robust procedure and generally, more useful (soluble) CRM197. A RhaT-deficient BL21 strain was produced by disrupting the rhaT gene using CRISPR/lambda RED method by inserting 5 nucleotides after the first 39 bases of the gene, creating 2 stop codons. The presence of the expected mutation was confirmed by the amplification and sequencing of the rhaT gene.

Example 11: Analysis of Purified CRM197

CRM197 produced as described in Example 6 and purified by standard methods, was analytically characterized and compared to commercial CRM197 (Pfenex CRM—Reagent Proteins, San Diego, CA) to assess the structural integrity, solubility, activity and conformational stability of CRM197 produced by the methods described herein.

Figure 13:
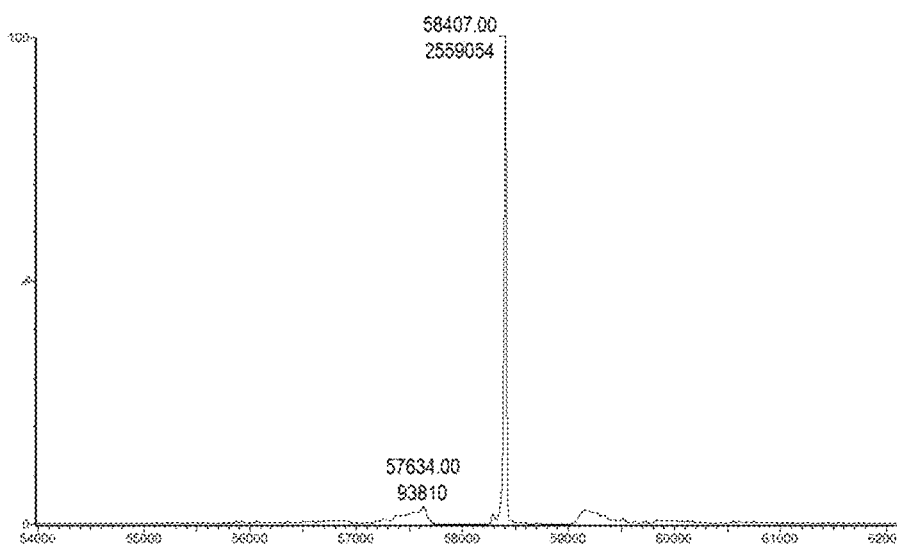
FIG. 13 depicts purified CRM197 intact mass analysis on LTQ-Orbitrap XL mass spectrometer.

The absence of signal sequence and the molecular weight of the purified CRM197 was verified by intact mass analysis. The predicted molecular weight of CRM197 is 58,413 Da and the weight calculated by intact mass analysis was 58,407 Da. Results of the intact mass analysis are shown in FIG. 13. Further, the CRM197 sequence was verified by nLC-MS/ MS analysis on the LTQ Orbitrap.

The secondary and tertiary structure of the purified CRM197 was verified using circular dichroism, as described in Analytical Biochemistry Volume 1994; 222(1): 176-184 and Nature Protocols 2006; 1(6): 2876-2890. This analysis confirmed that the purified CRM197 has the same secondary and tertiary structure as commercial CRM197.

The nuclease activity of the purified CRM197 was determined by incubating 2.5 μg of purified CRM197 with 500 ng of lambda DNA (λDNA, #N3011S, New England Biolabs) at a final volume of 10 μl in reaction buffer (10 mM Tris-HCl pH 7.6, 2.5 mM CaCl$_2$), 2.5 mM MgCl2) at 37° C. for 30 min, 1 h, 4 h, 8 h and 24 h. The reaction was stopped by adding 2 μl of gel loading dye containing 10 mM EDTA (Purple 6X, #B7024S, New England Biolabs) and analyzed using agarose gel electrophoresis (1% agarose). A negative control reaction was carried out containing λDNA in the same reaction buffer and exposed to the same reaction conditions in the absence of CRM197. After 24 h, the λDNA was almost fully digested in the test reaction but remained intact in the negative control.

The stability of the purified CRM197 was assessed by storing aliquots of semi-purified CRM197 at different temperatures, either in solution or as a dried sample, followed by visualization on an SDS PAGE gel to observe whether degradation was apparent. The semi-purified CRM197 was prepared by periplasmic extraction followed by anion-exchange chromatography. The solution samples were stored at room temperature, 4° C., -20° C. and -80° C. for up to 634 days. The dried sample was stored at 4° C. for up to 634 days. After 634 days storage at -20° C. or -80° C., the CRM197 in solution showed no visible signs of degradation. Only after three subsequent freeze-thaw cycles did the solution sample stored at -20° C. begin to show visible signs of degradation. Similarly, the dried sample stored at 4° C. for 634 days showed no visible signs of degradation.

Figure 14:
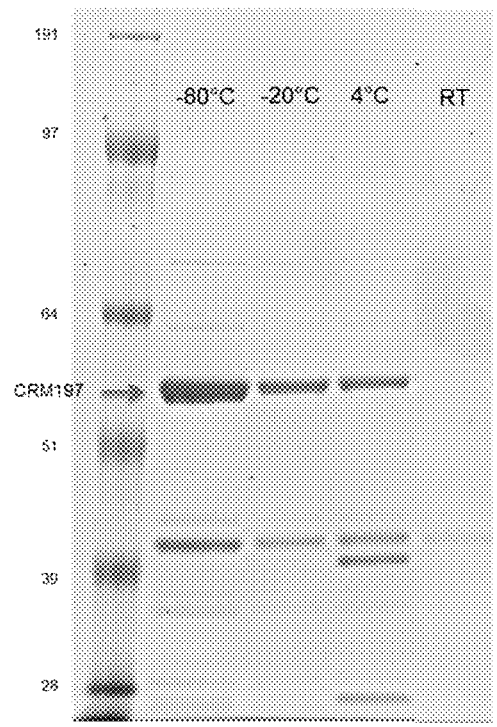
FIG. 14 depicts an SDS-PAGE gel of a purified CRM197 preparation after storage in solution for 634 days at −80° C., −20° C., 4° C., and room temperature, with the arrow indicating the CRM197 band.

Aliquots of CMR197 stored in solution at 4° C. or at room temperature were visibly intact after 194 days of storage. After 634 days of storage, the solution samples stored at 4° C. were partially degraded and the solution samples stored at room temperature appeared to be fully degraded. FIG. 14 shows solution samples of purified CRM197 run on an SDS-PAGE gel after 634 days storage at -80° C., -20° C., 4° C., and room temperature.

The analysis of the purified CRM197 confirms that CRM197 produced according to the methods described herein is equivalent to commercially available CRM197.

Example 12: Production of CRM197 in W3110

1—Bacterial Strains and Constructs

The bacterial strain used was *Escherichia coli* W3110 ΔrhaB with plasmid pD861-OmpT (mutated form)-CRM197, with the *E. coli* optimized CRM197 gene being under the control of rhaP$_{BAD}$ promoter, and having kanamycin resistance.

The rhamnose gene, encoding for the second enzyme allowing the catabolism of the rhamnose, L-rhamnulose kinase (rhaB), was mutated (inactivated) by inserting two nucleotides at position 221 of the gene, creating a detrimental frameshift in the sequence (FIG. 11, SEQ ID NO:8), as described above for *E. coli* BL21 strain ΔrhaB.

This mutation prevents the utilization of rhamnose as a carbon source by the cells.

2—Fermentation, Cell Lysis and Periplasmic Fraction Separation

The W3110 ΔrhaB strain was used for a fermentation experiment carried out in a Dasgip fermenter as described in Example 6, except without a post-induction feed, followed by cell lysis and periplasmic fraction separation, also as described in Example 6.

Figure 15:
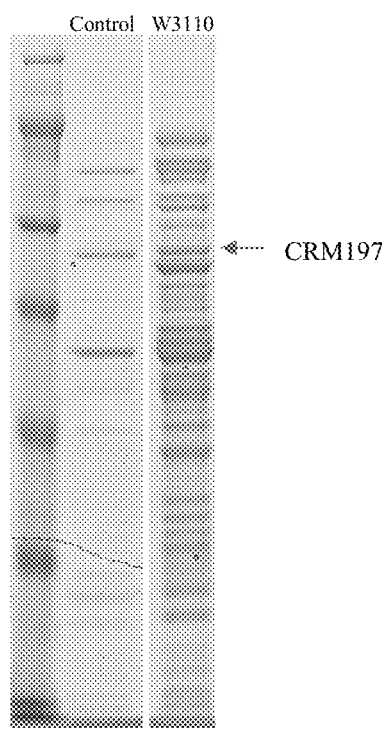
FIG. 15 depicts an SDS-PAGE gel of a CRM197 preparation produced using *E. coli* W3110 ΔrhaB cells. The left lane shows semi-purified CRM197 from BL21 ΔrhaB Dasgip fermentation while the right lane shows W3110 ΔrhaB periplasmic extraction after 28 hours of induction in Dasgip fermentor.

The periplasmic fraction was run on an SDS-PAGE gel (Bolt 8% Bis-Tris, MOPS buffer) to confirm CRM197 production (FIG. 15, right lane). CRM197 was present, but the level of expression was lower than with the BL21 ΔrhaB strain under the same conditions.

Although the present invention has been described hereinabove by way of specific embodiments thereof, it can be modified, without departing from the spirit and nature of the subject invention as defined in the appended claims.

What is claimed is:

1. An *Escherichia coli* (*E. coli*) cell comprising a defective sulA gene and a defective lon gene.

2. The *E. coli* cell of claim 1, wherein the *E. coli* cell is a BL21 strain cell.

3. The *E. coli* cell of claim 2, wherein the *E. coli* cell is a BL21 (DE3) strain cell.

4. The *E. coli* cell of claim 1, wherein the cell is defective in rhamnose catabolic pathway.

5. The *E. coli* cell of claim 4, wherein the cell comprises a defective rhaB gene.

6. The *E. coli* cell of claim 1, wherein the defective sulA gene comprises the nucleotide sequence set forth in SEQ ID NO: 10.

7. An expression system comprising the E. coli cell of claim 1, wherein the *E. coli* cell comprises a heterologous nucleic acid construct comprising an inducible promoter sequence operably linked to a nucleic acid molecule encoding a polypeptide.

8. The expression system of claim 7, wherein the inducible promoter is a rhamnose inducible promoter.

9. A method of gene targeting by homologous recombination, the method comprising introducing an in vivo double-strand break into a DNA molecule within an *E. coli* cell of claim 1, in the presence of a donor substrate DNA molecule.

* * * * *

```
                       SEQUENCE LISTING

Sequence total quantity: 10
SEQ ID NO: 1           moltype = AA  length = 21
FEATURE                Location/Qualifiers
source                 1..21
                       mol_type = protein
                       organism = Escherichia coli
SEQUENCE: 1
MKVKVLSLLV PALLVAGAAN A                                              21

SEQ ID NO: 2           moltype = DNA  length = 1671
FEATURE                Location/Qualifiers
source                 1..1671
                       mol_type = genomic DNA
                       organism = Corynebacterium diphtheriae
SEQUENCE: 2
atgaaagtta aggtgttgtc tttgttggtt cctgcattgt tggtcgctgg tgctgcaaat    60
gcgggtgcag atgacgtagt agacagcagc aaatcgttcg ttatggagaa tttcagcagc   120
taccacggta cgaagccggg ttacgtcgat tctattcaga agggcatcca gaaaccgaag   180
tccggtaccc aaggcaacta tgatgacgat tggaaagagt tttacagcac cgataacaaa   240
tatgacgcag cgggttatag cgttgataat gaaaatccgt tgtccggcaa agcaggcggc   300
gtggtcaaag tgacctatcc gggcctgacc aaagttctgg ccctgaaagt tgataacgcg   360
gaaaccatta gaaagagct gggtttgagc ttgacggaac cgctgatgga acaggtcggc   420
acggaagagt tcattaagcg ttttggcgat ggtgcttctc gcgttgttct gagcttgccg   480
tttgcggaag gtagcagcag cgtcgaatac attaacaatt gggagcaggc gaaagccctg   540
tccgttgagc tggagatcaa cttcgaaacc cgcgtaagc ggccaaga cgccatgtat     600
gagtatatgc cccaagcgtg tgctggcaac cgtgtgcgtc gcagcgtcgg tagcagcctg   660
tcgtgtatca atctggattg ggacgtgatt cgcgacaaaa ccaagaccaa aatcgaaagc   720
ctgaaagaac acggtccgat taagaataag atgagcgaat ctccgaataa gacggttagc   780
gaagagaagg cgaaacagta cctggaagag ttccaccaga ctgcgctgga acatccagag   840
ctgagcgagc tgaaaacggt gaccggtacc aacccagttt ttgctggtgc gaactatgcg   900
gcttgggcgg tcaacgtggc acaagtcatt gactccgaaa cggcagataa cctggagaaa   960
accactgcgg cgctgagcat cttgccgggt attggcagcg tgatgggcat cgcggacggt  1020
gccgtacacc ataacaccga agagatcgtg gcgcagagca tcgcgctgag ctctctgatg  1080
gtcgctcagg cgatcccgct ggtgggtgag ctggttgata ttggttttgc tgcttacaac  1140
tttgttgaga gcatcatcaa tctgttccag gtggtgcaca atagctacaa tcgtccggcg  1200
tacagccctg gtcacaaaac gcaaccgttc ctgcacgacg gttacgcggt ttcctggaat  1260
accgttgagg acagcattat tcgcaccggt ttccaaggcg agtctggcca tgacattaag  1320
atcacggcag aaaacacccc gctgccgatt gcgggtgtcc tgctgccgac gattccgggc  1380
aagctggatg tgaataagag caagacccac attagcgtta acggccgtaa gatccgtatg  1440
cgttgccgtg cgattgacgg tgacgtgacc ttttgccgcc ctaaaagccc ggtctacgtg  1500
ggtaatggtg tgcatgcgaa tctgcacgtt gccttccatc gtagcagctc cgagaaaatt  1560
cacagcaatg agatcagctc cgacagcatc ggtgtcctgg gctatcaaaa gaccgtcgat  1620
catacgaagg ttaactccaa gctgagcttg ttctttgaga tcaaaagcta a           1671

SEQ ID NO: 3           moltype = AA  length = 556
FEATURE                Location/Qualifiers
source                 1..556
                       mol_type = protein
                       organism = Corynebacterium diphtheriae
SEQUENCE: 3
MKVKVLSLLV PALLVAGAAN AGADDVVDSS KSFVMENFSS YHGTKPGYVD SIQKGIQKPK    60
SGTQGNYDDD WKEFYSTDNK YDAAGYSVDN ENPLSGKAGG VVKVTYPGLT KVLALKVDNA   120
ETIKKELGLS LTEPLMEQVG TEEFIKRFGD GASRVVLSLP FAEGSSSVEY INNWEQAKAL   180
SVELEINFET RGKRGQDAMY EYMAQACAGN RVRRSVGSSL SCINLDWDVI RDKTKTKIES   240
LKEHGPIKNK MSESPNKTVS EEKAKQYLEE FHQTALEHPE LSELKTVTGT NPVFAGANYA   300
AWAVNVAQVI DSETADNLEK TTAALSILPG IGSVMGIADG AVHHNTEEIV AQSIALSSLM   360
VAQAIPLVGE LVDIGFAAYN FVESIINLFQ VVHNSYNRPA YSPGHKTQPF LHDGYAVSWN   420
TVEDSIIRTG FQGESGHDIK ITAENTPLPI AGVLLPTIPG KLDVNKSKTH ISVNGRKIRM   480
RCRAIDGDVT FCRPKSPVYV GNGVHANLHV AFHRSSEKI HSNEISSDSI GVLGYQKTVD    540
HTKVNSKLSL FFEIKS                                                    556
```

```
SEQ ID NO: 4              moltype = DNA  length = 114
FEATURE                   Location/Qualifiers
source                    1..114
                          mol_type = genomic DNA
                          organism = Escherichia coli
SEQUENCE: 4
caccacaatt cagcaaattg tgaacatcat cacgttcatc tttccctggt tgccaatggc     60
ccatttttcct gtcagtaacg agaaggtcgc gaattcaggc gcttttttaga ctgg        114

SEQ ID NO: 5              moltype = DNA  length = 129
FEATURE                   Location/Qualifiers
source                    1..129
                          mol_type = genomic DNA
                          organism = Escherichia coli
SEQUENCE: 5
caccacaatt cagcaaattg tgaacatcat cacgttcatc tttccctggt tgccaatggc     60
ccatttttcct gtcagtaacg agaaggtcgc gaattcaggc gcttttttaga ctggtcgtaa   120
tgaacaatt                                                             129

SEQ ID NO: 6              moltype = DNA  length = 1683
FEATURE                   Location/Qualifiers
source                    1..1683
                          mol_type = genomic DNA
                          organism = Corynebacterium diphtheriae
SEQUENCE: 6
atgagcagaa aactgtttgc gtcaatctta ataggggcgc tactggggat aggggcccca     60
ccttcagccc atgcaggcgc tgatgatgtt gttgattctt ctaaatcttt tgtgatggaa    120
aacttttctt cgtaccacgg gactaaacct ggttatgtag attccattca aaaaggtata    180
caaaagccaa aatctggtac acaaggaaat tatgacgatg attggaaagg ttttatagt     240
accgacaata aatcgacgc tgcgggatac tctgtagata atgaaaaccc gctctctgga    300
aaagctggag gcgtggtcaa agtgacgtat ccaggactga cgaaggttct cgcactaaaa    360
gtggataatg ccgaaactat taagaaagag ttaggtttaa gtctcactga accgttgatg    420
gagcaagtcg gaacggaaga gtttatcaaa aggttcggtg atggtgcttc gcgtgtagtg    480
ctcagccttc ccttcgctga ggggagttct agcgttgaat atattaataa ctgggaacag    540
gcgaaagcgt taagcgtaga acttgagatt aattttgaaa cccgtggaaa acgtggccaa    600
gatgcgatgt atgagtatat ggctcaagcc tgtgcaggaa atcgtgtcag gcgatcagta    660
ggtagctcat tgtcatgcat aaatcttgat gggatgtca taggggataa aactaagaca    720
aagatagagt ctttgaaaga gcatggccct atcaaaaata aaatgagcga aagtcccaat    780
aaaacagtat ctgaggaaaa agctaaacaa tacctagaaa aatttcatca aacggcatta    840
gagcatcctg aattgtcaga acttaaaacc gttactggga ccaatcctgt attcgctggg    900
gctaactatg cggcgtgggc agtaaacgtt gcgcaagtta tcgatagcga aacagctgat    960
aatttggaaa agacaactgc tgctctttcg atacttcctg gtatcggtag cgtaatgggc   1020
attgcagacg gtgccgttca ccacaataca gaagagatag tggcacaatc aatagcttta   1080
tcgtctttaa tggttgctca agctattcca ttggtaggag agctagttga tattggtttc   1140
gctgcatata attttgtaga gagtattatc aatttatttc aagtagttca taattcgtat   1200
aatcgtcccg cgtattctcc ggggcataaa acacaaccat tcttcatga cgggtatgct   1260
gtcagttgga acactgttga agattcgata atccgaactg gttttcaagg ggagagtggg   1320
cacgacataa aaattactgc tgaaaatacc ccgcttccaa tcgcgggtgt cctactaccg   1380
actattcctg gaaagctgga cgttaataag tccaagactc atatttccgt aaatggtcgg   1440
aaaataagga tgcgttgcag agctatagac ggtgatgtaa cttttttgtcg ccctaaatct   1500
cctgttttatg ttggtaacgg tgtgcatgcg aatcttcacg tggcatttca cagaagcgc   1560
tcggagaaaa ttcattctaa tgaaatttcc tcggattcca taggcgttct tgggtaccag   1620
aaaaacagtag atcacaccaa ggttaattct aagctatcgc tatttttttga aatcaaaagc   1680
tga                                                                   1683

SEQ ID NO: 7              moltype = AA  length = 560
FEATURE                   Location/Qualifiers
source                    1..560
                          mol_type = protein
                          organism = Corynebacterium diphtheriae
SEQUENCE: 7
MSRKLFASIL IGALLGIGAP PSAHAGADDV VDSSKSFVME NFSSYHGTKP GYVDSIQKGI     60
QKPKSGTQGN YDDDWKGFYS TDNKYDAAGY SVDNENPLSG KAGGVVKVTY PGLTKVLALK    120
VDNAETIKKE LGLSLTEPLM EQVGTEEFIK RFGDGASRVV LSLPFAEGSS SVEYINNWEQ    180
AKALSVELEI NFETRGKRGQ DAMYEYMAQA CAGNRVRRSV GSSLSCINLD WDVIRDKTKT    240
KIESLKEHGP IKNKMSESPN KTVSEEKAKQ YLEEFHQTAL EHPELSELKT VTGTNPVFAG    300
ANYAAWAVNV AQVIDSETAD NLEKTTAALS ILPGIGSVMG IADGVHHNT EEIVAQSIAL     360
SSLMVAQAIP LVGELVDIGF AAYNFVESII NLFQVVHNSY NRPAYSPGHK TQPFLHDGYA    420
VSWNTVEDSI IRTGFQGESG HDIKITAENT PLPIAGVLLP TIPGKLDVNK SKTHISVNGR    480
KIRMRCRAID GDVTFCRPKS PVYVGNGVHA NLHVAFHRSS SEKIHSNEIS SDSIGVLGYQ    540
KTVDHTKVNS KLSLFFEIKS                                                 560

SEQ ID NO: 8              moltype = DNA  length = 1462
FEATURE                   Location/Qualifiers
source                    1..1462
                          mol_type = genomic DNA
                          organism = Escherichia coli
SEQUENCE: 8
atgaccttc gcaattgtgt cgccgtcgat ctcggcgcat ccagtgggcg cgtgatgctg     60
```

```
gcgcgttacg agcgtgaatg ccgcagcctg acgctgcgcg aaatccatcg ttttaacaat    120
gggctgcata gtcagaacgg ctatgtcacc tgggatgtgg atagcctgga aagtgccatt    180
cgcctttggat taaacaaggt gtgcgaggaa gggattcgta tcgcgatagc attgggattg   240
atacctgggg cgtggacttt gtgctgctcg accaacaggg tcagcgtgtg ggcctgcccg    300
ttgcttatcg cgatagccgc accaatggcc taatggcgca ggcacaacaa caactcggca    360
aacgcgatat ttatcaacgt agcggcatcc agtttctgcc cttcaatacg ctttatcagt    420
tgcgtgcgct gacggagcaa caacctgaac ttattccaca cattgctcac gctctgctga    480
tgccggatta cttcagttat cgcctgaccg gcaagatgaa ctgggaatat accaacgcca    540
cgaccacgca actggtcaat atcaatagcg acgactggga cgagtcgcta ctggcgtgga    600
gcggggccaa caaagcctgg tttggtcgcc cgacgcatcc gggtaatgtc ataggtcact    660
ggatttgccc gcagggtaat gagattccgg tggtcgccgt tgccagccat gataccgcca    720
gcgcggttat cgcctcgccg ttaaacggtt cacgcgccgc ttatctctct tctggcacct    780
ggtcattgat gggcttcgaa agccagacgc catttaccaa tgacacggcg ctggcagcca    840
acatcaccaa tgaaggcggg gcggaaggtc gctatcgggt gctgaaaaat attatgggct    900
tatggctgct tcagcgagtg ctacaggagc ggcaaatcaa cgatctcccg gcgcttatcg    960
ccgcgacaca ggcacttccg gcctgccgct tcatcatcaa tcccaatgac gatcgcttta   1020
ttaaccctga cgagatgtgc agcgaaattc aggctgcgtg tcgggaaatg gcgcaaccga   1080
tcccagaaag tgatgctgaa ctggcgcgct gtattttcga cagtctggcg ttgctgtatg   1140
ccgatgtgtt gcatgagctg gcgcagctac gcggtgaaga tttctcgcaa ctgcatattg   1200
tcggcggcgg ctgccagaac acgctgctca accagctatg tgccgatgcc tgcggtattc   1260
gggtgatcgc cgggcctgtt gaagcctcga cgctcggcaa tatcggcatc cagttaatga   1320
cgctggatga actcaacaat gtggatgatt tccgtcaggt cgtcagcacc accgcgaatc   1380
tgaccaccgtt taccctaat cctgacagtg aaattgccca ctatgtggcg ctgattcact   1440
ctacacgaca gacaaaggag ct                                            1462

SEQ ID NO: 9           moltype = DNA  length = 89
FEATURE                Location/Qualifiers
misc_feature           1..89
                       note = Synthetic oligomer
source                 1..89
                       mol_type = other DNA
                       organism = synthetic construct
SEQUENCE: 9
gtgcgatctt cctgaggccg atactgtcgt cgtcccctca tgaacctgaa tgcacggtta     60
cgatgcgccc atctacacca acgtgacct                                       89

SEQ ID NO: 10          moltype = DNA  length = 511
FEATURE                Location/Qualifiers
source                 1..511
                       mol_type = genomic DNA
                       organism = Escherichia coli
SEQUENCE: 10
atgtacactt caggctatgc acatcgttct tcgtcgttct catccgcagc aagtaaaatt     60
gcgcgtgtct ctacggaaaa cactacagcc tgaacctgac agtgaagttg tctatcgcga    120
agatcagccc atgatgacgc aacttctact gttgccattg ttacagcaac tcggtcagca    180
atcgcgctgg caactctggt taacaccgca acaaaaactg agtcgggaat gggttcaggc    240
atctgggcta cccttaacga aagtaatgca gattagccag ctctcccctt gccacactgt    300
ggagtcaatg gttcgcgctt tacgcacggg caattacagt gtggtgatcg gttggttggc    360
agatgatttg actgaagaag agcatgctga acttgttgat gcggcaaatg aaggtaacgc    420
tatgggggttt attatgcgtc cggtaagcgc atcctctcac gccacgagac aactttccgg    480
gctaaaaatt cactctaatt tgtatcatta a                                   511
```